US012365048B2

(12) United States Patent
Takata

(10) Patent No.: US 12,365,048 B2
(45) Date of Patent: Jul. 22, 2025

(54) OUTPUT ADJUSTMENT DEVICE FOR LITHOTRIPSY APPARATUS, SUCTION FORCE GENERATION METHOD, AND ATTRACTING METHOD

(71) Applicant: OLYMPUS CORPORATION, Tokyo (JP)

(72) Inventor: Yuhei Takata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 463 days.

(21) Appl. No.: 17/735,381

(22) Filed: May 3, 2022

(65) Prior Publication Data

US 2022/0296300 A1 Sep. 22, 2022

Related U.S. Application Data

(63) Continuation of application No. PCT/JP2020/020408, filed on May 22, 2020.
(Continued)

(51) Int. Cl.
*B23K 26/06* (2014.01)
*A61B 18/26* (2006.01)
(Continued)

(52) U.S. Cl.
CPC .......... *B23K 26/0622* (2015.10); *A61B 18/26* (2013.01); *A61P 13/12* (2018.01);
(Continued)

(58) Field of Classification Search
CPC ........ B23K 26/0622; B23K 26/0853; B23K 26/40; A61P 13/12; H01S 3/06716; H01S 3/1616; A61B 2018/263
(Continued)

(56) References Cited

U.S. PATENT DOCUMENTS

2006/0287662 A1  12/2006  Berry et al.
2008/0015556 A1   1/2008  Chan et al.
(Continued)

FOREIGN PATENT DOCUMENTS

CA   2 656 391 A1   1/2008
CA   2 893 494 A1  11/2015
(Continued)

OTHER PUBLICATIONS

Gonzalez, D.A., et al., "Comparison of single, dual, and staircase temporal pulse profiles for reducing stone retropulsion during thulium fiber laser lithotripsy in an in vitro stone phantom model", Proceedings of SPIE10852, Therapeutics and Diagnostics in Urology 2019, 108520E(Feb. 26, 2019), doi:10.1117/12.2514052.
(Continued)

*Primary Examiner* — Michael J Lau
(74) *Attorney, Agent, or Firm* — Scully, Scott, Murphy & Presser, P.C.

(57) ABSTRACT

Provided is an output adjustment device for a laser lithotripsy apparatus including: a processor including hardware, the processor being configured to: pulse a laser beam; adjust an output of the pulsed laser beam; monotonically increase the output of the laser beam as a first period to generate a bubble binding body containing a plurality of bubbles from a laser emission end; monotonically decrease the output of the laser beam with a gradient larger than a predetermined gradient as a second period following the first period to cause the bubble binding body to disappear so that a crushing target is attracted to the laser emission end; and before the bubble binding body is generated, raise a liquid temperature in a region where the bubble binding body is generated by generating the bubbles and causing the bubbles to disappear.

20 Claims, 30 Drawing Sheets

Related U.S. Application Data

(60) Provisional application No. 62/934,019, filed on Nov. 12, 2019.

(51) Int. Cl.
| | |
|---|---|
| *A61P 13/12* | (2006.01) |
| *B23K 26/0622* | (2014.01) |
| *B23K 26/08* | (2014.01) |
| *B23K 26/40* | (2014.01) |
| *H01S 3/067* | (2006.01) |
| *H01S 3/16* | (2006.01) |

(52) U.S. Cl.
CPC .......... *B23K 26/0853* (2013.01); *B23K 26/40* (2013.01); *H01S 3/06716* (2013.01); *H01S 3/1616* (2013.01); *A61B 2018/263* (2013.01)

(58) Field of Classification Search
USPC ........................................................ 606/2.5
See application file for complete search history.

(56) References Cited

U.S. PATENT DOCUMENTS

| | | | |
|---|---|---|---|
| 2008/0015557 A1 | 1/2008 | Chan et al. | |
| 2011/0087201 A1 | 4/2011 | Chan et al. | |
| 2011/0098691 A1 | 4/2011 | Chan et al. | |
| 2015/0100048 A1* | 4/2015 | Hiereth | A61B 18/26 606/2.5 |
| 2015/0313444 A1* | 11/2015 | Wolf | A61B 17/22004 600/103 |
| 2015/0342678 A1* | 12/2015 | Deladurantaye | A61F 9/008 606/5 |
| 2016/0051125 A1 | 2/2016 | Wolf | |
| 2017/0354464 A1 | 12/2017 | Waisman et al. | |
| 2018/0092693 A1 | 4/2018 | Falkenstein et al. | |
| 2018/0206918 A1 | 7/2018 | Waisman et al. | |
| 2019/0183573 A1 | 6/2019 | Waisman et al. | |
| 2019/0233321 A1* | 8/2019 | Ellison | B23K 26/009 |
| 2019/0298449 A1 | 10/2019 | Khachaturov et al. | |
| 2021/0113268 A1 | 4/2021 | Waisman et al. | |
| 2021/0137596 A1 | 5/2021 | Falkenstein et al. | |
| 2021/0378745 A1 | 12/2021 | Fukushima et al. | |

FOREIGN PATENT DOCUMENTS

| | | |
|---|---|---|
| EP | 2 840 999 B1 | 3/2016 |
| EP | 3 412 239 A1 | 12/2018 |
| JP | 2008/541883 A | 11/2008 |
| JP | 2013-031701 A | 2/2013 |
| JP | 2013527601 A * | 6/2013 |
| JP | 2017-515561 A | 6/2017 |
| JP | 2019-531605 A | 10/2019 |
| WO | 2006/128038 A2 | 11/2006 |
| WO | 2008/009005 A2 | 1/2008 |
| WO | 2013/159793 A1 | 10/2013 |
| WO | 2015/171289 A1 | 11/2015 |
| WO | 2017/212404 A1 | 12/2017 |
| WO | 2018/067530 A1 | 4/2018 |
| WO | 2020/033121 A1 | 2/2020 |
| WO | 2020/174686 A1 | 9/2020 |

OTHER PUBLICATIONS

Blackmon, R.L., et al., "Enhanced thulium fiber laser lithotripsy using micro-pulse train modulation", Journal of Biomedical Optics, vol. 17(2), 028002, SPIE, doi:10.1117/1.JBO.17.2.028002.
International Search Report dated Jul. 21, 2020 received in PCT/JP2020/020408.
1 Japanese Office Action dated Apr. 25, 2013 received in 2021-555784.

* cited by examiner

FIG. 27

SUCTION SUCCESS RATE

| | Z, mm | 2.5 | 2.5 | 2.5 | 2.5 |
| | X, mm | 1 | 1.5 | 2 | |
|---|---|---|---|---|---|
| 1 | Sq | 3/3 | 2/3 | 3/3 | |
| 2 | DT | 1/3 | 0/3 | 0/3 | |
| 3 | AT | 3/3 | 3/3 | 0/3 | |
| 4 | MP | 0/3 | 0/3 | 0/3 | |

SUCTION VELOCITY (mm/sec)

| | Z, mm | 2.5 | 2.5 | 2.5 |
| | X, mm | 1 | 1.5 | 2 |
|---|---|---|---|---|
| 1 | Sq | 14±10 | 7±7 | 4±0 |
| 2 | DT | 15 | N/A | N/A |
| 3 | AT | 10±5 | 5±2 | N/A |
| 4 | MP | N/A | N/A | N/A |

OUTPUT ADJUSTMENT DEVICE FOR LITHOTRIPSY APPARATUS, SUCTION FORCE GENERATION METHOD, AND ATTRACTING METHOD

CROSS-REFERENCE TO RELATED APPLICATION

The application claims the benefit of priority from U.S. Provisional Patent Application No. 62/934,019, filed on Nov. 12, 2019, the entire contents of which are incorporated herein by reference.

This is a continuation of International Application PCT/JP2020/020408, filed on May 22, 2020, which is hereby incorporated by reference herein in its entirety.

TECHNICAL FIELD

The present invention relates to an output adjustment device for a laser lithotripsy apparatus, a suction force generation method, and an attracting method.

BACKGROUND ART

Conventionally, as a treatment for urolithiasis, a laser lithotripsy treatment for crushing stones by irradiating the stones with a laser beam. A Ho: YAG laser and a Thulium fiber laser are used as lasers for crushing stones. When sizes of stones are small, the stones may move significantly backward (retropulsion) due to bubbles and an ablation force generated by the laser irradiation, or the stones may migrate away from a direction of the laser irradiation (migration). The retropulsion is also likely to occur in a method of crushing the stones by bringing an optical fiber for irradiating the laser beam into contact with the stones. For this reason, it is difficult to aim at the stones.

In a situation where a stone moves, a technique called popcorn lithotripsy has been used in which the stone is crushed while moving around in the renal pelvis or the renal calyx. However, the popcorn lithotripsy is said to have lower crushing efficiency than the method of crushing the stone by bringing the optical fiber into contact with the stone.

In recent years, a phenomenon called "Suction Effect" has been paid attention especially in the Thulium fiber laser. As such a suction effect, it has been confirmed that distant stones are attracted in a diagonal direction or a frontal direction toward the optical fiber, but the detailed mechanism has not been clarified so far. When such suction effect can be controlled appropriately, it is considered that moving stones can be crushed by manipulation or that a behavior of stones can be controlled in the course of popcorn lithotripsy.

In PTL 1, as shown in FIG. 29, when the rising of the output pulse is blunt by shortly increasing or decreasing rather than monotonically increasing, the optical energy is absorbed by water before it reaches the stone to generate a bubble as small as possible. Then, the remaining optical energy hits the stone for crushing, whereby a stone retropulsion (backward movement) is reduced and crushing efficiency is improved.

PTL 2 is an international application published after U.S. Provisional Application No. 62/934,019, filed on Nov. 12, 2019, which the application claims the benefit of priority. In a technique disclosed in PTL 2, the influence of backward movement of a stone is reduced by a first pulse with low output. Then, after raising from the first pulse to a second pulse with high output, the stone is crushed by the second pulse having a square shape. In PTL 2, a laser pulse including the first pulse with low output and the second pulse with high output is used, and an interval is provided between these first and second pulses during which a bubble generated by the first pulse reaches the stone and disappears. Herein, a suction effect is described in which the stone moves in a frontal direction toward a laser emission end when the bubble disappears. In NPL 1, as shown in FIG. 30, it is reported that in a stepped pulse shape, a suction effect phenomenon is observed in which a stone phantom once separated from the fiber after irradiation with optical energy goes back to the fiber tip.

CITATION LIST

Patent Literature

{PTL 1} European Patent No. 2840999 B1
{PTL 2} PCT International Publication No. 2020/033121

Non Patent Literature

{NPL 1} David A. Gonzalez, Nicholas C. Giglio, Layton A. Hall, Viktoriya Vinnichenko, and Nathaniel M. Fried "Comparison of single, dual, and staircase temporal pulse profiles for reducing stone retropulsion during thulium fiber laser lithotripsy in an in vitro stone phantom model", Proc. SPIE 10852, Therapeutics and Diagnostics in Urology 2019, 108520E (26 Feb. 2019)

SUMMARY OF INVENTION

One aspect of the present invention provides an output adjustment device for a laser lithotripsy apparatus including: a processor including hardware, the processor being configured to: pulse a laser beam; adjust an output of the pulsed laser beam; monotonically increase the output of the laser beam as a first period to generate a bubble binding body containing a plurality of bubbles from a laser emission end; monotonically decrease the output of the laser beam with a gradient larger than a predetermined gradient as a second period following the first period to cause the bubble binding body to disappear so that a crushing target is attracted to the laser emission end; and before the bubble binding body is generated, raise a liquid temperature in a region where the bubble binding body is generated by generating the bubbles and causing the bubbles to disappear.

Another aspect of the present invention provides a suction force generation method executed by a processor, the method including: emitting a pulse-like laser beam from a laser emission end in a liquid to generate bubbles and cause the bubbles to disappear so as to raise a liquid temperature in a region where the bubbles are caused to disappear; monotonically increasing an output of the laser beam to generate a bubble binding body containing the bubbles in the region where the liquid temperature is raised; and monotonically decreasing the output of the laser beam with a gradient larger than a predetermined gradient to cause the bubble binding body to disappear so as to generate a suction force in a frontal direction of the laser emission end.

Further another aspect of the present invention provides an attracting method including: inserting an endoscope into a specimen; disposing a laser emission end toward a target to be attracted; displaying an image data acquired by the endoscope in a display; setting a waveform of a laser beam on the basis of the image data; monotonically increasing an output of the laser beam as a first period to generate a bubble binding body containing a plurality of bubbles from the laser emission end; and monotonically decreasing the output of the laser beam with a gradient larger than a predetermined gradient as a second period following the first period to cause the bubble binding body to disappear so that the target to be attracted is attracted to the laser emission end.

BRIEF DESCRIPTION OF DRAWINGS

FIG. 27 is a view showing a result of suction success rate and a suction velocity.

DESCRIPTION OF EMBODIMENTS

A laser lithotripsy apparatus, a laser lithotripsy system, and a laser lithotripsy method according to an embodiment of the present invention will be described below with reference to the drawings.

Figure 1:
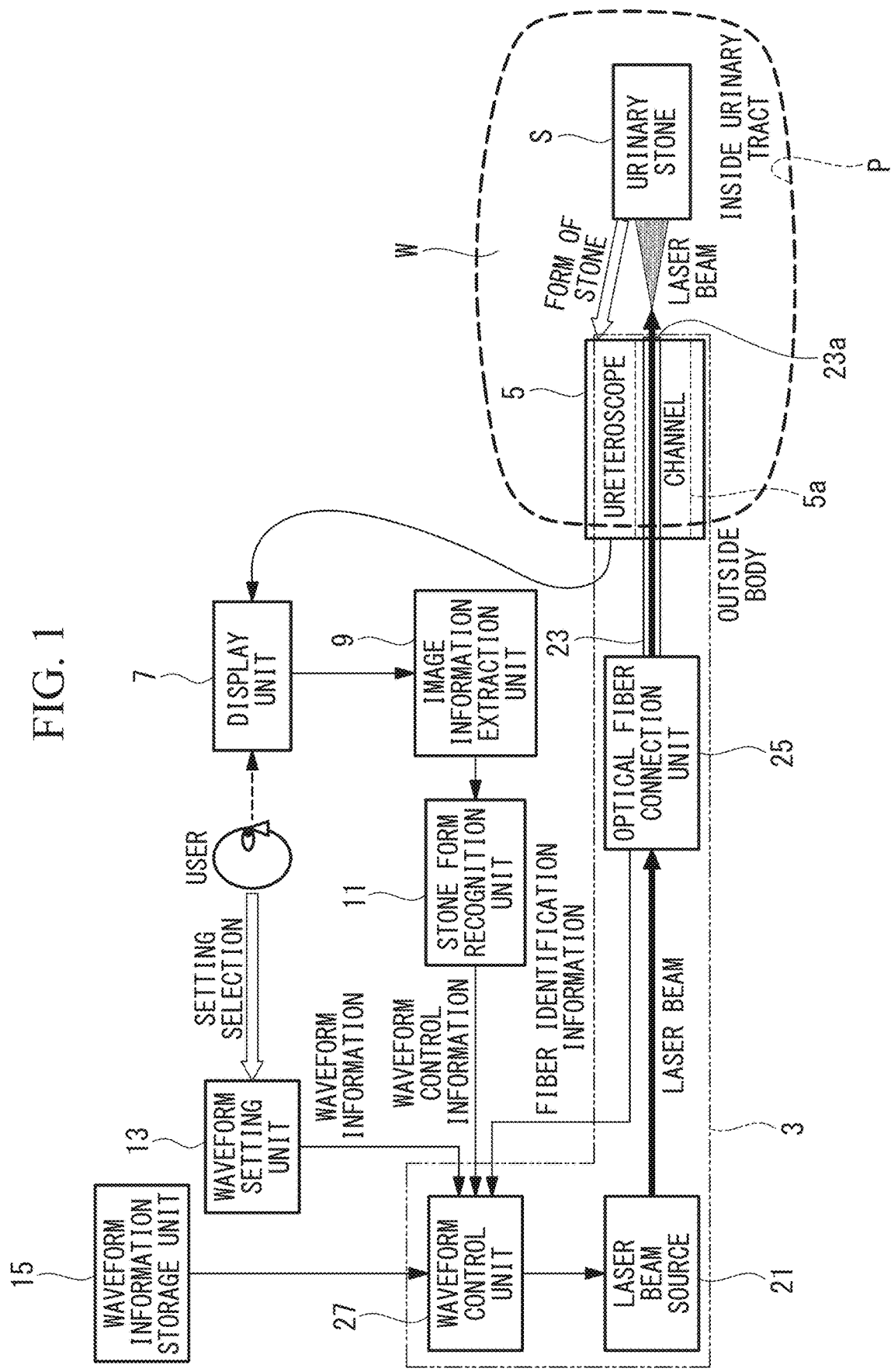
FIG. 1 is a schematic block diagram of a laser lithotripsy system according to an embodiment of the present invention.
Figure 2:
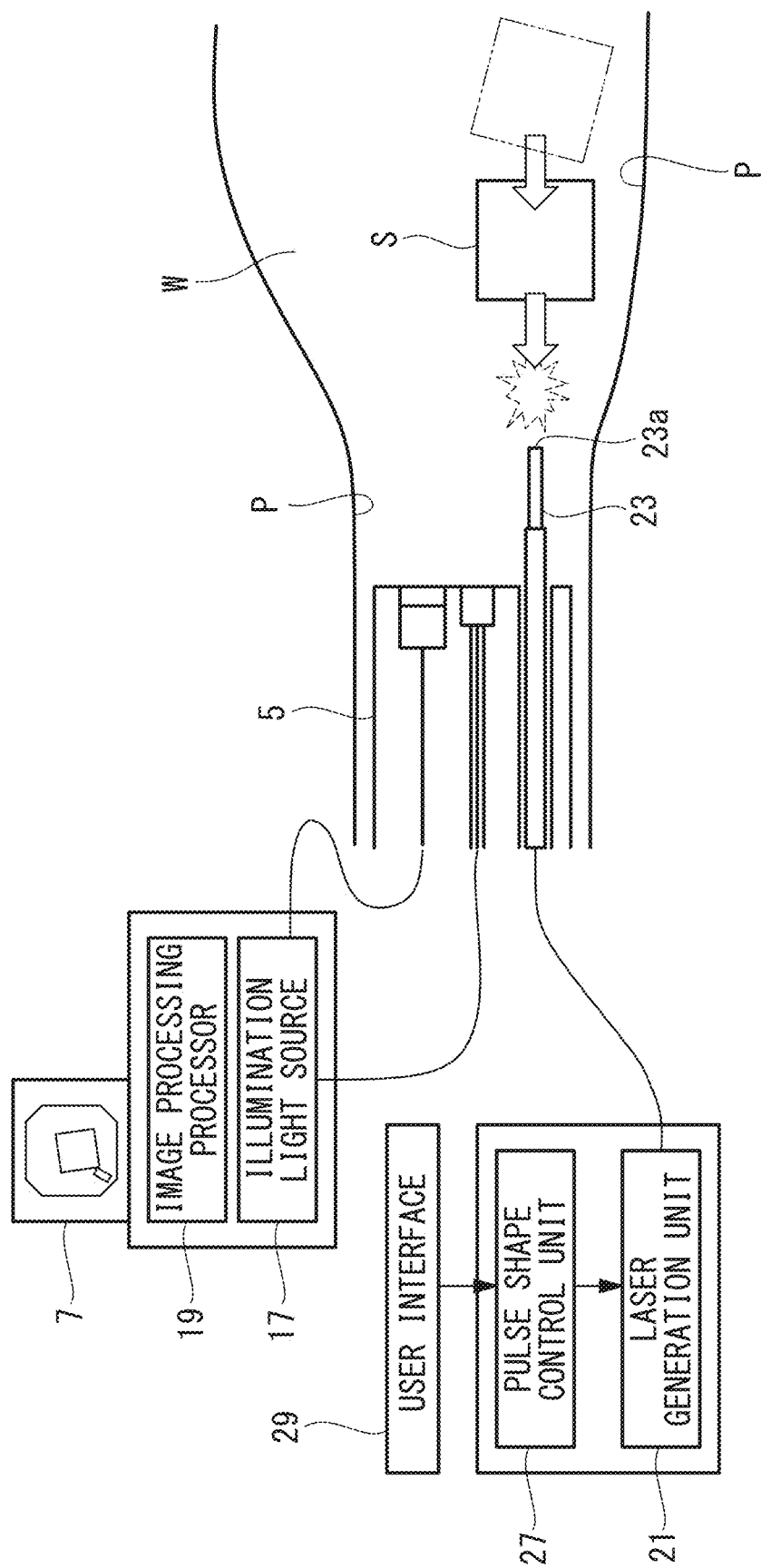
FIG. 2 is another schematic block diagram illustrating the laser lithotripsy system shown in FIG. 1.

A laser lithotripsy system 1 according to the present embodiment includes a laser lithotripsy apparatus 3, a rigid or flexible ureteroscope 5, a display unit 7, an image information extraction unit 9, a stone form recognition unit 11, a waveform setting unit 13, and a waveform information storage unit 15 as shown in FIGS. 1 and 2.

The laser lithotripsy apparatus 3 includes a laser beam source 21, an optical fiber 23, an optical fiber connection unit 25, and a waveform control unit (pulse generation unit, output adjustment unit) 27. In FIG. 2, reference numeral 29 indicates a user interface.

As the laser beam source 21, for example, a Thulium Fiber Laser (TLR-50/500-QCW-AC-Y16, IPG Photonics) can be used. Alternatively, as the laser beam source 21, for example, Holmium: YAG laser, Thulium: YAG laser, Erbium: YAG laser, Pulsed dye laser, or Q-switched Nd: YAG laser may be used.

The optical fiber 23 may be, for example, either a single mode fiber or a multimode fiber, or may be a fiber having a double clad structure. Further, the optical fiber 23 may be added with thulium. The optical fiber 23 is guided into a urinary tract P through a channel 5a of the ureteroscope 5. The urinary tract P is filled with urine and a solution W such as water or saline solution. The optical fiber 23 includes a fiber tip (laser emission end) 23a that emits a guided laser beam.

The optical fiber connection unit 25 reads information of the connected optical fiber 23. Then, the optical fiber connection unit 25 transmits fiber identification information including characteristics such as a core diameter and NA of the optical fiber 23 to the waveform control unit 27.

The ureteroscope 5 observes a form of urinary stone (stone) S. As shown in FIG. 2, for example, the ureteroscope 5 is connected with an illumination light source 17 that generates illumination light and an image processing processor (image acquisition unit) 19 that generates a ureteroscope image on which the urinary stone S is imaged. The image generated by the image processing processor 19 is displayed on the display unit 7.

A user can confirm, from the ureteroscope image displayed on the display unit 7, whether a bubble B (see FIG. 3) generated by a laser beam has reached the urinary stone S. Then, the user makes a determination by looking at the ureteroscope image, and thus can set a waveform of the laser beam using the waveform setting unit 13.

The image information extraction unit 9 extracts the form of the urinary stone S based on the ureteroscope image generated by the ureteroscope 5.

The stone form recognition unit 11 recognizes the form of the urinary stone S extracted by the image information extraction unit 9 to generate waveform control information, and transmits the generated waveform control information to the waveform control unit 27.

The waveform setting unit 13 sets the waveform of the laser beam selected by the user. The waveform setting unit 13 transmits waveform information indicating the set waveform to the waveform control unit 27.

The waveform information storage unit 15 stores wavelength information of the laser beam source 21 and waveform information used to generate an appropriate waveform based on the wavelength information.

The waveform control unit 27 acquires desired waveform information from the waveform information storage unit 15, based on at least one of the fiber identification information sent from the optical fiber connection unit 25, the waveform information sent from the waveform setting unit 13, and the waveform control information sent from the stone form recognition unit 11. Then, the waveform control unit 27 controls oscillation of the laser beam source 21 based on the acquired waveform information. The processing by the waveform control unit 27 may be performed by at least one processor including hardware.

Figure 3:
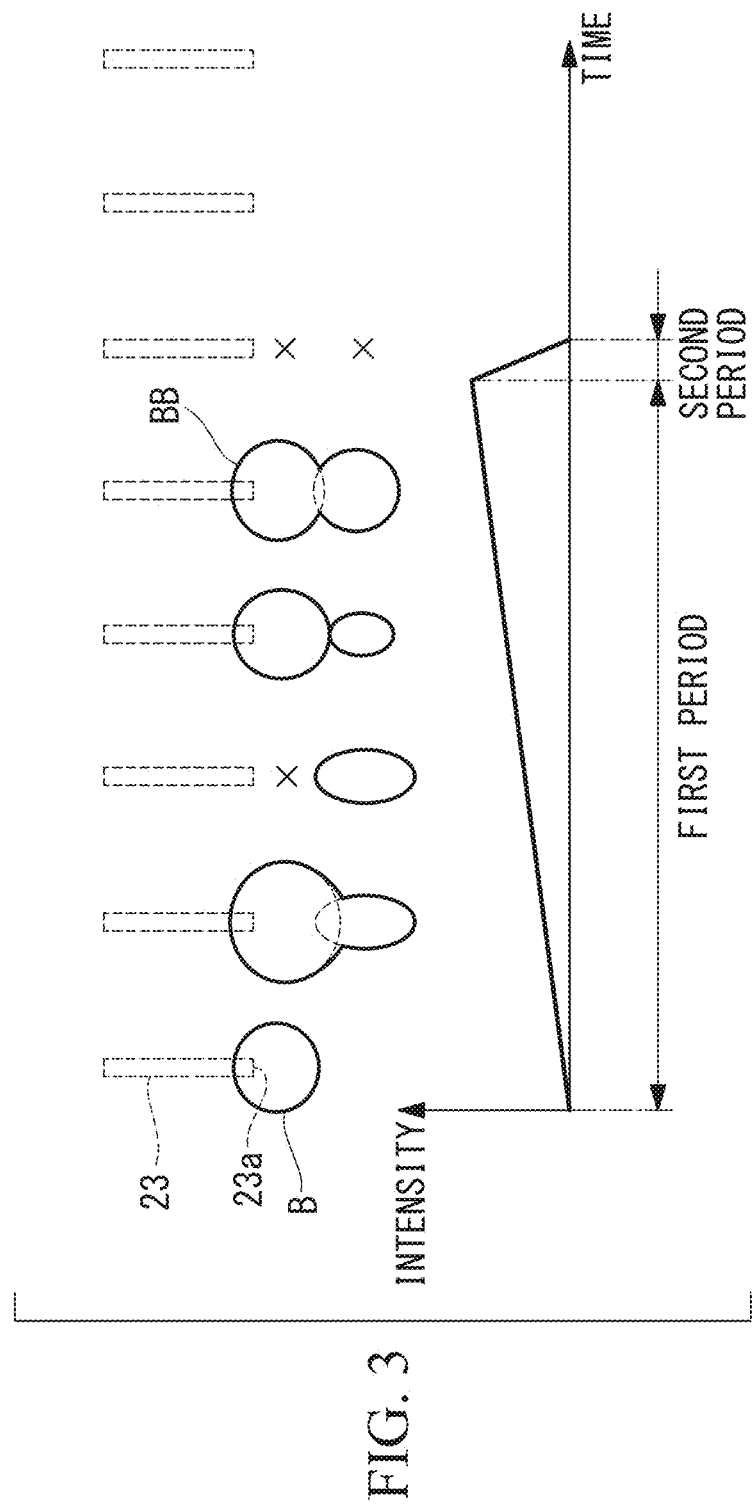
FIG. 3 is a view showing a relation between a pulse shape of a laser beam and a shape of a bubble.

The waveform control unit 27 shapes a pulse shape of the laser beam into an ascending triangle pulse, for example. Specifically, the waveform control unit 27 first monotonically increases an output of the laser beam oscillated from the laser beam source 21 as shown in FIG. 3. Thus, a plurality of bubbles B are continuously generated from the fiber tip 23a by the pulse-like laser beam emitted from the fiber tip 23a. Further, it is preferable to couple the fiber tip 23a and the urinary stone S by a bubble binding body BB formed by binding of the plurality of bubbles B. A period during which the output of the laser beam is monotonically increased is defined as a first period. In the first period, the output of the laser beam may be monotonically increased with a gradient smaller than a predetermined gradient.

Subsequently, the waveform control unit 27 switches the output of the laser beam after the first period, and monotonically reduces the output with a gradient larger than the predetermined gradient. Thereby, the bubble binding body BB disappears, and thus a suction force is generated. Then, the urinary stone S is attracted to the fiber tip 23a by the suction force. A period during which the output of the laser beam is monotonically reduced is defined as a second period.

A repetition frequency of the laser beam is preferably 1.7 kHz or more and 3.0 kHz or less. The repetition frequency of the laser beam may be 1.7 kHz or more and 2.5 kHz or less.

Further, the repetition frequency of the laser beam may be 2.5 kHz or more and 3.0 kHz or less. The gradient of the output of the laser beam may be in a range of 0.625 to 5.0 W/µs. For example, in the first period during which the output of the laser beam has a right ascending waveform, the output is gently and monotonically increased with a gradient of 2.5 W/µsec or less. Further, subsequently, in the second period during which the output of the laser beam has a right descending waveform, the output is sharply and monotonically reduced with a gradient of 2.5 W/µsec or more, and the output is preferably stopped.

For example, a function generator (WF1974, NF) can be used to generate the pulse shape. The above-described processing by the image information extraction unit 9, the stone form recognition unit 11, and the waveform control unit 27 may be executed by at least one processor including hardware.

Figure 4:
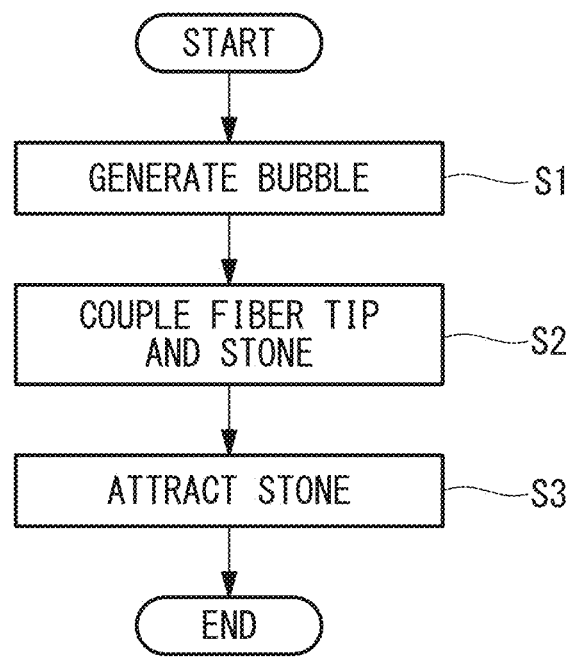
FIG. 4 is a flowchart illustrating a laser lithotripsy method according to the embodiment of the present invention.

Next, the laser lithotripsy method according to the present embodiment includes, for example, as shown in a flowchart of FIG. 4, step S1 in which a pulse-like laser beam is emitted from the fiber tip 23a to continuously generate the bubble binding body BB formed by binding of the plurality of bubbles B from the fiber tip 23a and step S3 in which the urinary stone S is attracted to the fiber tip 23a by a suction force generated by disappearing of the bubble binding body BB. Step S2 in which the fiber tip 23a and the urinary stone S are coupled by the bubble binding body BB may be included between step S1 and step S3.

Next, operations of the laser lithotripsy system 1 and the laser lithotripsy method according to the present embodiment will be described.

When a stone is crushed by the laser lithotripsy system 1 and the laser lithotripsy method, after the optical fiber 23 is connected to the optical fiber connection unit 25, the fiber tip 23a is disposed toward the urinary stone S in the solution W. Then, a distance from the fiber tip 23a to the urinary stone S is maintained within a predetermined range. Fiber identification information is transmitted from the optical fiber connection unit 25 to the waveform control unit 27.

Next, Illumination light is irradiated from the illumination light source 17 toward the urinary stone S. In addition, a laser beam is generated from the laser beam source 21. The oscillated laser beam is incident on the optical fiber 23 through the optical fiber connection unit 25. The laser beam guided by the optical fiber 23 is emitted from the fiber tip 23a toward the urinary stone S.

Subsequently, an image of the urinary stone S is generated by the image processing processor 19, and the generated image is displayed on the display unit 7. The user sets a waveform of the laser beam using the waveform setting unit 13, based on the ureteroscope image displayed by the display unit 7. Waveform information indicating the set waveform is transmitted to the waveform control unit 27.

Further, the image information extraction unit 9 extracts a form of the urinary stone S, based on the generated ureteroscope image. Then, the stone form recognition unit 11 generates, based on the extracted form of the urinary stone S, waveform control information. The generated waveform control information is transmitted to the waveform control unit 27.

The waveform control unit 27 acquires desired waveform information from the waveform information storage unit 15, based on at least one of the fiber identification information sent from the optical fiber connection unit 25, the waveform information sent from the waveform setting unit 13, and the waveform control information sent from the stone form recognition unit 11, and oscillation of the laser beam source 21 is controlled based on the acquired waveform information.

Figure 5:
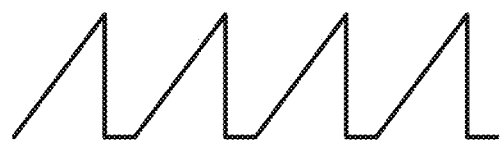
FIG. 5 is a view showing an example of a pulse shape.

Specifically, as shown in FIG. 5, the output of the laser beam emitted from the laser beam source 21 is switched to the first period in which the output monotonically increases with a gradient smaller than the predetermined gradient and the second period in which the output monotonically decreases with a gradient larger than the predetermined gradient, and is alternately repeated in the order of the first period and the second period.

Figure 6:
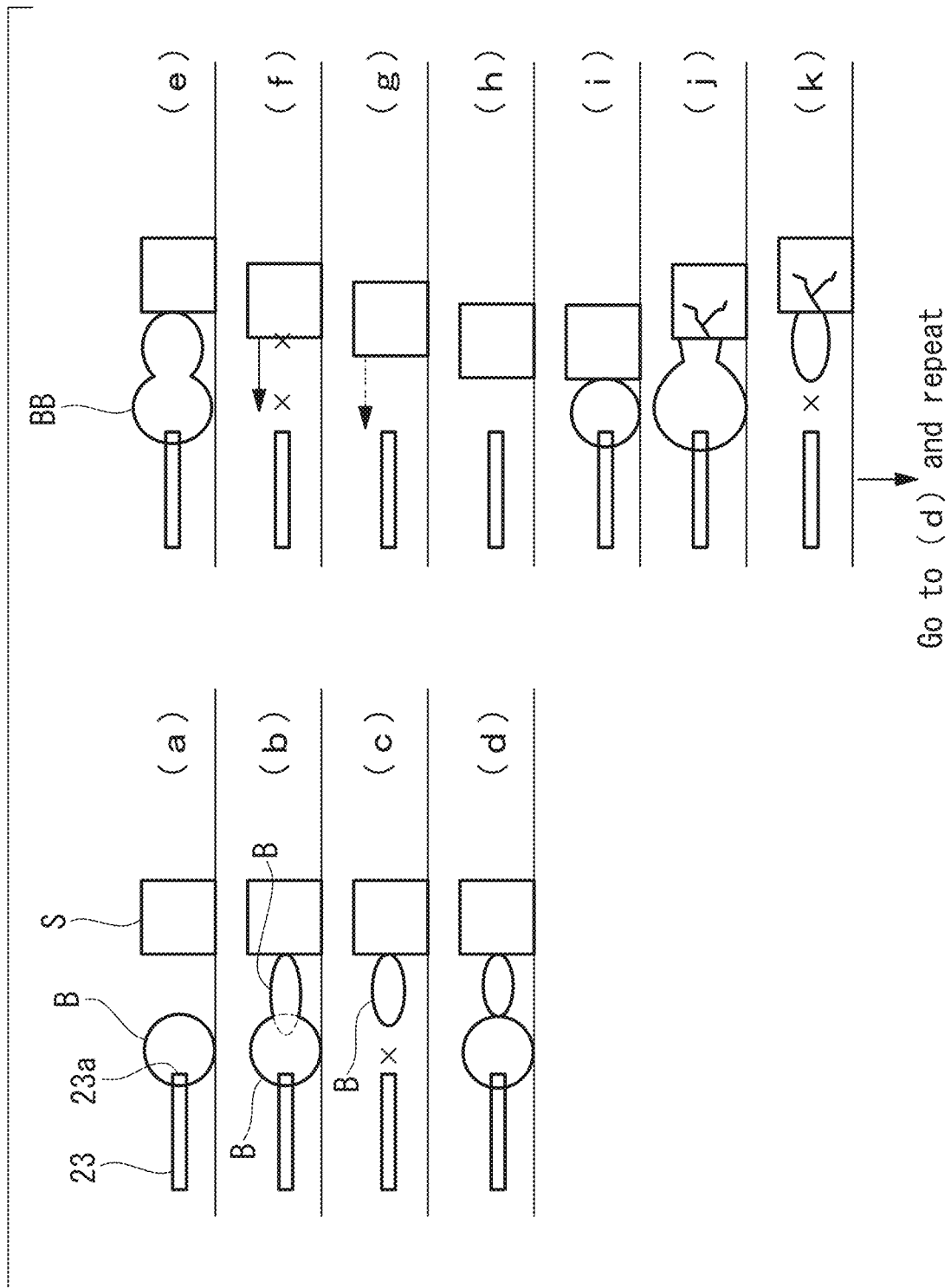
FIG. 6 is a view illustrating shapes of bubbles and behavior of stones.

Thereby, for example, as shown in FIG. 6, first, a bubble B is generated from the fiber tip 23a (a state of (a) in FIG. 6) by emission of the laser beam with the output monotonically increasing with the gradient smaller than the predetermined gradient in the first period. Then, a second bubble B is generated from a tip of the bubble B (a state of (b) in FIG. 6) when the bubble B becomes a certain size due to the laser beam being emitted while the output is monotonically increasing.

Next, the second bubble B remains (a state of (c) in FIG. 6) when the first bubble B contracts as the bubble B is cooled by the solution W. Further, a new bubble B is generated from the fiber tip 23a (a state of (d) in FIG. 6) when the laser beam is emitted while the output is monotonically increasing. When the new bubble B binds to the second bubble B as the new bubble B grows, a bubble binding body BB is formed (a state of (e) in FIG. 6) in which the two bubbles B are bound.

Subsequently, the output of the laser beam is switched from the first period to the second period. When the output of the laser beam monotonically decreases with the gradient larger than the predetermined gradient by the switching to the second period, the bubble binding body BB disappears (a state of (f) in FIG. 6). A suction force is generated by disappearing of the bubble binding body BB, and thus the urinary stone S is attracted to the fiber tip 23a (a state of (g) in FIG. 6).

Next, when the laser beam is emitted (a state of (h) in FIG. 6), a bubble B is generated from the fiber tip 23a (a state of (i) in FIG. 6). Then, when the second bubble B generated from the bubble B comes into contact with the urinary stone S due to the laser beam being emitted while the output is monotonically increasing, the laser beam passes through the bubble B, and thus the urinary stone S is irradiated with the laser beam (a state of (j) in FIG. 6).

Next, when the first bubble B contracts, the second bubble B remains (a state of (k) in FIG. 6). Then, the same steps as in the states (d) to (k) in FIG. 6 are repeated until the urinary stone S is crushed to a desired size. The urinary stone S is crushed by a steam explosion due to a temperature rise caused by absorption of the energy of the irradiated laser beam by water existing in the urinary stone S, or by a thermochemical change due to absorption of the energy of the laser beam by the urinary stone S itself.

As described above, according to the laser lithotripsy apparatus 3, the laser lithotripsy system 1, and the laser lithotripsy method according to the present embodiment, an attraction action generated by the disappearing of the bubble binding body BB can be efficiently utilized. Thereby, the urinary stone S can be prevented from moving in a direction away from the fiber tip 23a due to the impact of the laser beam, and the urinary stone S can be irradiated with the laser beam within a certain distance from the fiber tip 23a. Therefore, the suction effect can be effectively used, and the urinary stone S can be efficiently irradiated with the laser beam.

In the present embodiment, as described above, in the first period in which the output of the laser beam has the right ascending waveform, the output is gently and monotonically increased with the gradient of 2.5 W/μsec or less, and in the second period in which the output of the laser beam has the right descending waveform, the output is sharply and monotonically reduced with a gradient of 2.5 W/μsec or more, and the output is preferably stopped.

On the other hand, as Comparative Example of the present embodiment, when the output is rapidly monotonically increased with a gradient of more than 2.5 W/μsec in the first period and the output is gently monotonically reduced with a gradient of less than 2.5 W/μsec in the subsequent second period, although it differs slightly depending on components of the medium (solution W), a plurality of bubbles B are not formed, or a plurality of discrete bubbles B not coupled to each other are generated, whereby little suction effect was observed.

Further, when the output is rapidly monotonically increased with a gradient of more than 2.5 W/μsec in the first period and then the output gradient is changed to a plateau (including a horizontal or flat top of a square pulse), the bubble B became fragile. Then, a plurality of bubbles B did not exist at the same time, or the bubbles B disappeared in different orders without being coupled to each other.

Further, even when the output is gently monotonically increased with a gradient of 2.5 W/μsec or less in the first period, and the output is gently monotonically reduced with a gradient of 2.5 W/μsec or less in the subsequent second period, the coupled bubble B disappeared fragmentarily or gradually, and a sufficient suction effect was not observed.

A time from when the pulse of the right ascending waveform is applied until the bubbles B are coupled to each other differs depending on the medium and parameters other than the waveform. Therefore, when measurement is performed by irradiating a dummy or an actual urinary stone S with a pulse having the same medium environment and parameters as at the time of use, it is possible to acquire the time from when the pulse of the right ascending waveform is applied until the bubbles B are coupled to each other.

The present embodiment can be modified into the following configuration.

Figure 7:
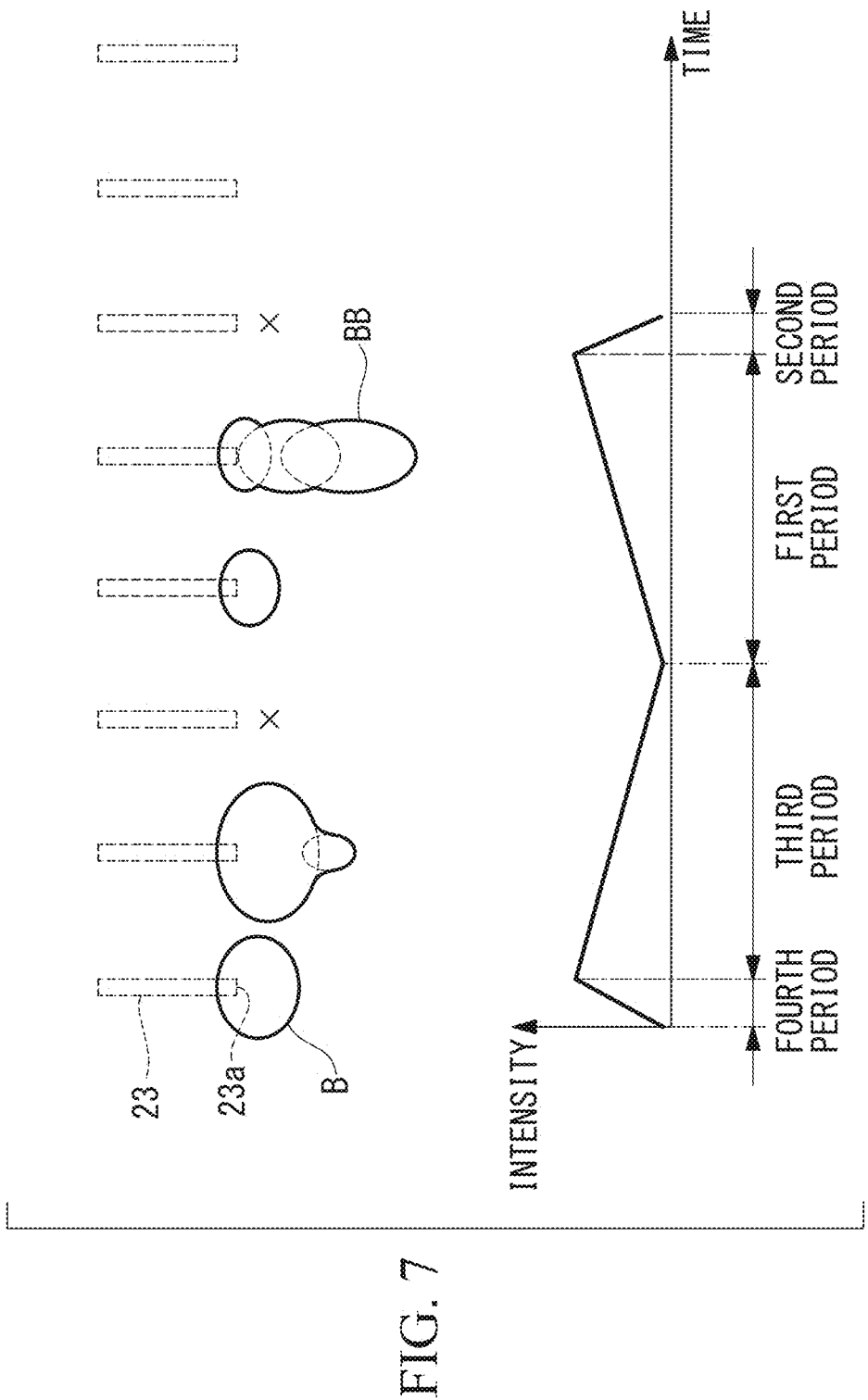
FIG. 7 is a view showing a relation between a pulse shape of a laser beam and a shape of a bubble according to a modification of the embodiment of the present invention.

In the present embodiment, the ascending triangle pulse consisting of the first period and the second period has been adopted. As a modification, for example, as shown in FIG. 7, the waveform control unit 27 may monotonically reduce the output of the laser beam with a gradient smaller than a predetermined gradient before the first period. A period in which the output of the laser beam is monotonically reduced before the first period is defined as a third period.

Further, the waveform control unit 27 may monotonically increase the output of the laser beam with a gradient larger than a predetermined gradient before the third period. A period in which the output of the laser beam is monotonically increased before the third period is defined as a fourth period.

In this case, the output of the laser beam monotonically increases with a gradient larger than the predetermined gradient in the fourth period, and thus a first bubble B is rapidly generated from the fiber tip 23a. Next, the output of the laser beam monotonically decreases with a gradient smaller than the predetermined gradient in the third period, whereby a second bubble B is further generated from the first bubble B, and then both the bubbles B disappear.

The pulse waveform has an M-shape in which the ascending triangle pulse described in the present embodiment and the descending triangle pulse obtained by left-right reversion of the ascending triangle pulse are coupled in the order of the descending triangle pulse and the ascending triangle pulse. The left half of the M-shaped pulse, that is, the descending triangle pulse is formed by an ascending waveform corresponding to the fourth period in which the output monotonically increases with a gradient of 2.5 W/μsec or more and a right descending waveform corresponding to the subsequent third period in which the output monotonically decreases with a gradient of 1.25 W/μsec or more and 2.5 W/μsec or less. The right half of the M-shaped pulse is equal to the waveform of the ascending triangle pulse described in the present embodiment.

Operations of the laser lithotripsy system 1 and the laser lithotripsy method having the above-described configuration will be described.

Figure 8:
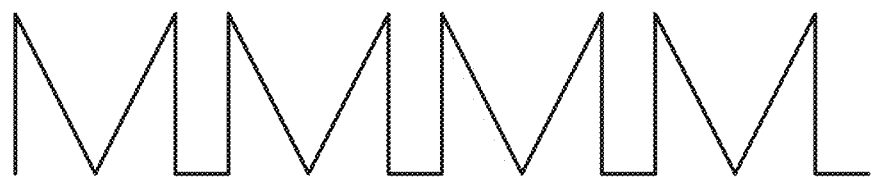
FIG. 8 is a view showing an example of the pulse shape according to the modification.

When a stone is crushed by the laser lithotripsy system 1 and the laser lithotripsy method according to the modification, as shown in FIG. 8, the output of the laser beam is switched to the fourth period, the third period, the first period, and the second period by the waveform control unit 27, and is repeated in the order of the fourth period, the third period, the first period, and the second period.

Figure 9:
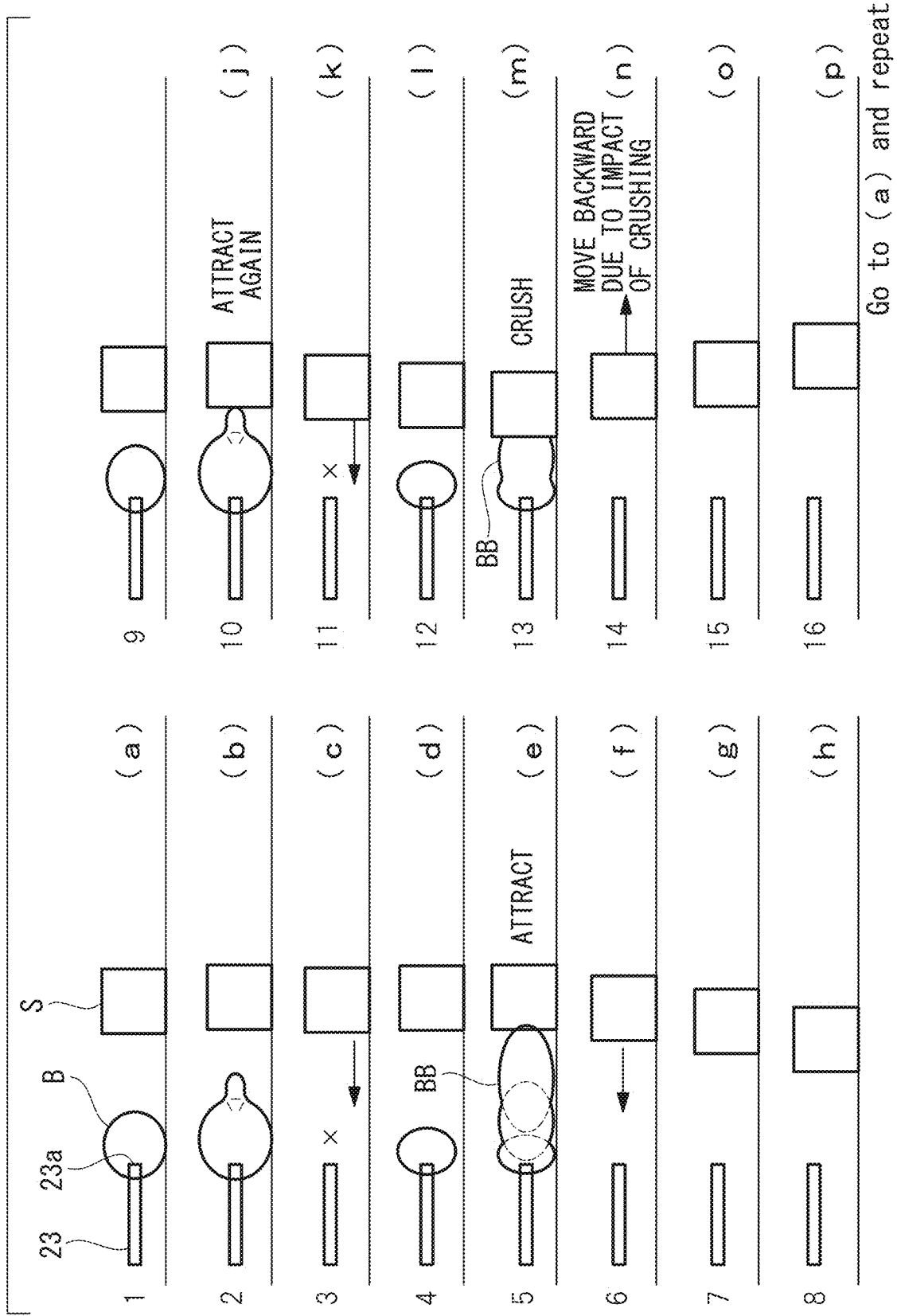
FIG. 9 is a view illustrating shapes of bubbles and behavior of stones according to the modification.

Thereby, for example, as shown in FIG. 9, first, a bubble B is rapidly generated from the fiber tip 23a (a state of (a) in FIG. 9) by emission of the laser beam with the output monotonically increasing with the gradient larger than the predetermined gradient in the fourth period.

Next, the output of the laser beam is switched from the fourth period to the third period. When the laser beam with the output monotonically decreasing with a gradient smaller than the predetermined gradient is emitted by the switching to the third period, the bubble B gradually increases, and a second bubble B is generated from the tip of the bubble B (a state of (b) in FIG. 9). Then, when both of the bubbles B disappear, a suction force is generated, and thus the urinary stone S is attracted to the fiber tip 23a (a state of (c) in FIG. 9).

Next, the output of the laser beam is switched from the third period to the first period. When the laser beam with the output monotonically increasing with a gradient smaller than the predetermined gradient is emitted by the switching to the first period, a bubble B is generated from the fiber tip 23a (a state of (d) in FIG. 9).

In the first period in this case, the bubble B generated in the fourth period and the third period warms the solution W on an optical path corresponding to an optical path in which the laser beam propagates while maintaining a luminous flux, whereby a plurality of continuous bubbles B are generated as a lump from the fiber tip 23a. Then, a bubble binding body BB coupling the fiber tip 23a and the urinary stone S is rapidly formed (a state of (e) in FIG. 9).

Next, the output of the laser beam is switched from the first period to the second period. When the laser beam with the output monotonically decreasing with a gradient larger than the predetermined gradient is emitted by the switching to the second period, the bubble binding body BB disappears. Thereby, a suction force is generated, and thus the urinary stone S is attracted to the fiber tip 23a (states of (f), (g), and (h) in FIG. 9).

Next, the output of the laser beam is switched from the second period to the fourth period. When the laser beam with the output monotonically increasing with a gradient larger than the predetermined gradient is emitted by the switching to the fourth period, a bubble B is rapidly generated at the fiber tip 23a (a state of (i) in FIG. 9).

Next, the output of the laser beam is switched from the fourth period to the third period. When the laser beam with the output monotonically decreasing with a gradient smaller than the predetermined gradient is emitted by the switching to the third period, the bubble B gradually increases, and a second bubble B is generated from the tip of the bubble B (a state of (j) in FIG. 9). Then, when both of the bubbles B disappear, a suction force is generated, and thus the urinary stone S is attracted to the fiber tip 23a (a state of (k) in FIG. 9).

Next, when the laser beam is emitted, a bubble B is generated from the fiber tip 23a (a state of (l) in FIG. 9). In this period, the output of the laser beam may or may not monotonically increase as in the first period.

Also in this case, the bubble B generated in the fourth period and the third period warms the solution W on the optical path of the laser beam, whereby a plurality of continuous bubbles B are generated as a lump from the fiber tip 23a. Then, a bubble binding body BB coupling the fiber tip 23a and the urinary stone S is rapidly formed (a state of (m) in FIG. 9). Thereby, the laser beam passes through the bubble binding body BB, and thus the urinary stone S is irradiated with the laser beam again.

When the urinary stone S moves in a direction away from the fiber tip 23a due to the impact of the laser beam (states of (n), (o), and (p) in FIG. 9), the same steps as in the states (a) to (p) in FIG. 9 are repeated. Then, the laser beam is repeatedly irradiated, and thus the urinary stone S is crushed to a desired size.

As described above, according to this modification, the bubble B is rapidly generated in the fourth period before the first and second periods, and the solution on the optical path of the laser beam is warmed by the third period, whereby the fiber tip 23a and the urinary stone S are rapidly coupled by the bubble binding body BB in the subsequent first period.

In this modification, the left half of the M-shaped pulse, that is, the descending triangle pulse is formed by an ascending waveform corresponding to the fourth period in which the output monotonically increases with a gradient of 5 W/μsec or more and a right descending waveform corresponding to the subsequent third period in which the output monotonically decreases with a gradient of 25 W/μsec or more and 2.5 W/μsec or less.

The ascending waveform in the fourth period has a steep gradient with no room for bubble B to be formed. Further, in the third period of the right descending waveform following the ascending waveform, a bubble B having a relatively large size is generated when the preceding steep ascending waveform turns downward. Then, the output monotonically decreases with a gentle gradient in the third period, and thus the bubble B is maintained until the end of the descending waveform. Therefore, the medium is heated through the bubble B in the third period. Further, the output monotonically decreases with a gradient of 1.25 W/μsec or more and 2.5 W/μsec or less in the third period, and thus the bubble B is difficult to be burst, whereby the bubble B is maintained without a retropulsion action on the urinary stone S.

The bubble B generated in the course of the descending triangle pulse in the fourth and third periods disappears once when the output starts to increase by switching from the descending triangle pulse in the left half of the M-shaped pulse to the ascending triangle pulse in the right half. However, in the course of monotonically increasing the output in the subsequent first period, after two or three bubbles B are typically generated in quick succession, the plurality of bubbles B are coupled without disappearing. After that, as described above, a suction effect can be obtained in a short time by changing from the rise of the ascending triangle pulse to the steep descending pulse of the second period.

On the other hand, as Comparative Example of this modification, when the output is rapidly monotonically increased with a gradient of less than 2.5 W/μsec in the fourth period, which is the initial ascending waveform of the left half of the M-shaped pulse, one or more bubbles B may be generated instantaneously regardless of the size, and this suggests that the urinary stone S may move distantly.

In addition, when the output is rapidly monotonically decreased with a gradient of more than 2.5 W/μsec in the third period, which is the right descending waveform following the initial ascending waveform of the left half of the M-shaped pulse, only a plurality of discrete bubbles B are formed without disappearing or being coupled in the middle of the descending waveform, and the heating of the medium through the bubbles B is insufficient.

Further, when the gradient is close to a plateau (including a horizontal or flat top of a square pulse), the bubble B became fragile. Then, a plurality of bubbles B did not exist at the same time, or the bubbles B disappeared in different orders without being coupled to each other.

In the present embodiment, the stone form recognition unit 11 may function as a calculation unit that calculates the distance between the bubble B and the urinary stone S based on the image. Further, information regarding the calculated distance may be displayed by the display unit 7. From the image information displayed by the display unit 7 and the information regarding the distance calculated by the stone form recognition unit 11, the user can easily grasp the distance between the fiber tip 23a and the urinary stone S.

In the present embodiment, the laser beam is repeatedly emitted while having an interval, but the laser beam may be repeatedly emitted without having an interval.

The present embodiment indicates the example of application to the ureter, but an endoscope may be used to acquire an image from any organ that can cause stones in the body, such as a bile duct or a kidney. The laser lithotripsy according to compositions of the stone generated in each organ is preferably performed while looking at the image. The aspect of the laser lithotripsy apparatus using an endoscope may refer to the international application No. PCT/JP2019/007928, entitled Lithotripsy apparatus and Lithotripsy system.

EXAMPLE

Examples of the laser lithotripsy apparatus 3, the laser lithotripsy system 1, and the laser lithotripsy method according to the above-described embodiment will be described below.

Method

In this Example, four types of pulse shapes having the same pulse energy, that is, a square pulse (Squre: Sq), descending triangle pulse (Descending Triangle: DT), an ascending triangle pulse (Ascending Triangle: AT), an M-shaped pulse (M-shaped Pulse: MP) were used as a comparison target. Optical energy was transmitted using an optical fiber (HLFDBX0270c, Dornier MedTech) with a core diameter of 270 um. Table 1 indicates pulse shape parameters, and FIG. 10 shows pulse shapes of respective pulses.

TABLE 1

| Pulse shape parameter | | | | | | |
|---|---|---|---|---|---|---|
| Pulse energy (J) | Pulse rate (Hz) | Average power (W) | Total energy (J) | Pulse shape | Pulse length (ms) | Power sequence (W) |
| 0.2 | 80 | 16 | 16 | Sq | 0.4 | 500 |
|  |  |  |  | DT | 0.8 | 500-0 |
|  |  |  |  | AT | 0.8 | 0-500 |
|  |  |  |  | MP | 0.728 | 500-50-500* |

Figure 10:
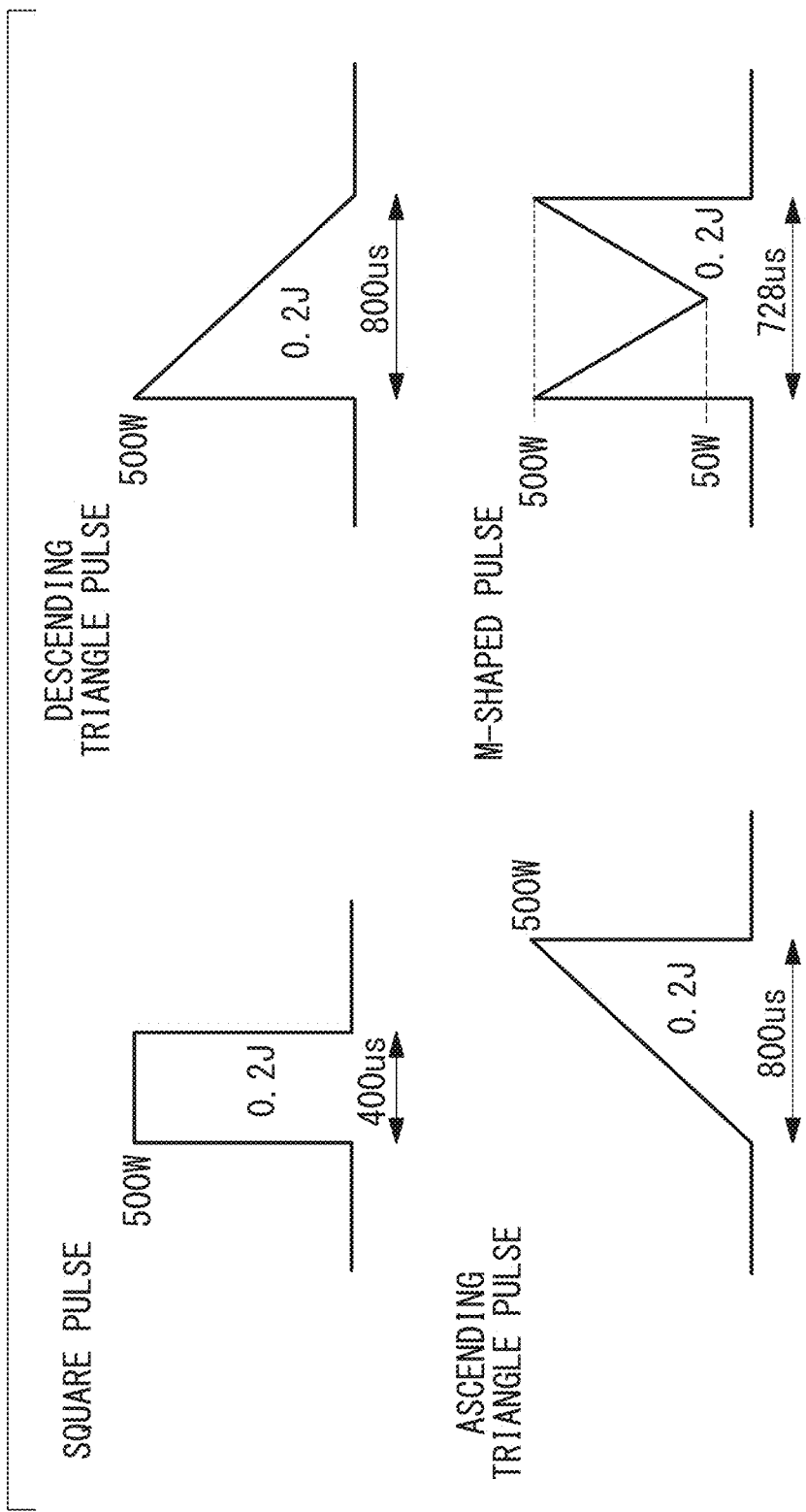
FIG. 10 is a view showing four types of pulse shapes.

The parameters other than the pulse shape shown in FIG. 10, for example, the pulse energy (J), the average power (W), and the pulse width (μs), are selected in this Example, and referred to as examples of suitable parameters. In other words, all the laser beam pulses adopted in this Example have an average power of 500 W and a pulse energy of 0.2 J, and the pulse width is different depending on each of the pulse shapes. In other words, according to the related art, the square pulse is 400 μs, both the descending triangle pulse and the ascending triangle pulse are 800 μs, and the M-shaped pulse is 728 μs. The M-shaped pulse has an average power of 50 W, not zero, at the lowest point in a center, which corresponds to half the pulse width. In these pulse shapes, the gradient of the pulse output relative to behavior of bubble formation and disappearance can be defined by the average power and the pulse width. Regardless of the value of each parameter specified in FIG. 10, the present invention can be appropriately modified based on the scope of the invention described in the present description.

Figure 11:
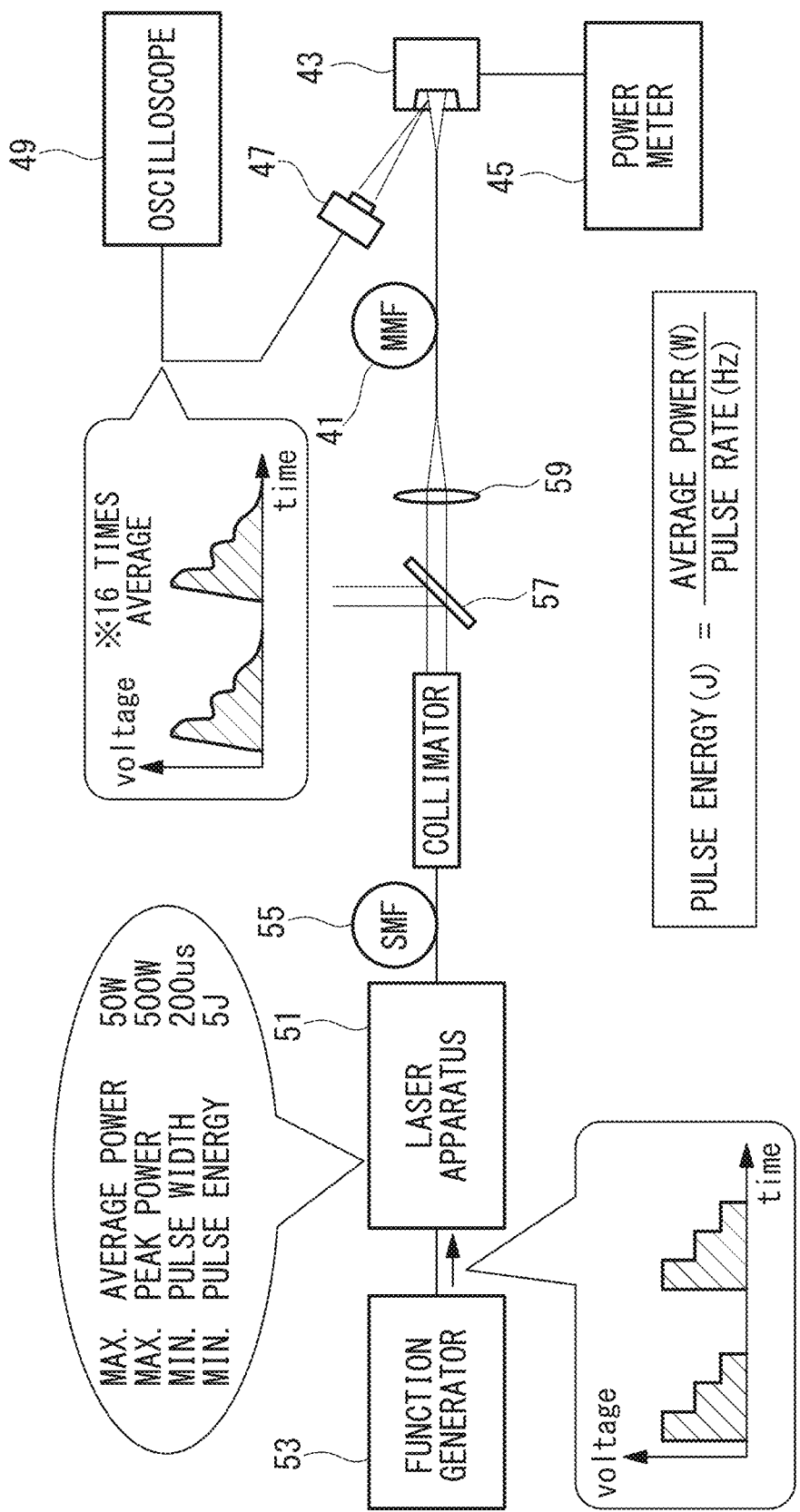
FIG. 11 is a schematic block diagram showing an example of a system that measures a pulse energy.

As shown in FIG. 11, an actual average power irradiated from an optical fiber (272 μm-core MMF (HLFDBX0270C, Dornier)) 41 was measured by a power sensor (S322C, Thorlabs) 43 and a power meter (PM100D, Thorlabs) 45.

Further, the pulse shape was measured by an optical detector (DET10D/M, Thorlabs) 47. An output waveform of the optical detector 47 was acquired by digitally averaging 16 times with an oscilloscope 49. The pulse energy (J) was calculated by dividing the average power (W) by the pulse rate (Hz). In FIG. 11, reference numeral 55 indicates an optical fiber (Single Mode Fiber), reference numeral 57 indicates a dichroic mirror (DMLP1800L, Thorlabs R=0.0225 (@λ=1.94 μs)), and reference numeral 59 indicates a condensing lens (LA5763-D, Thorlabs f=50 mm).

Figure 12:
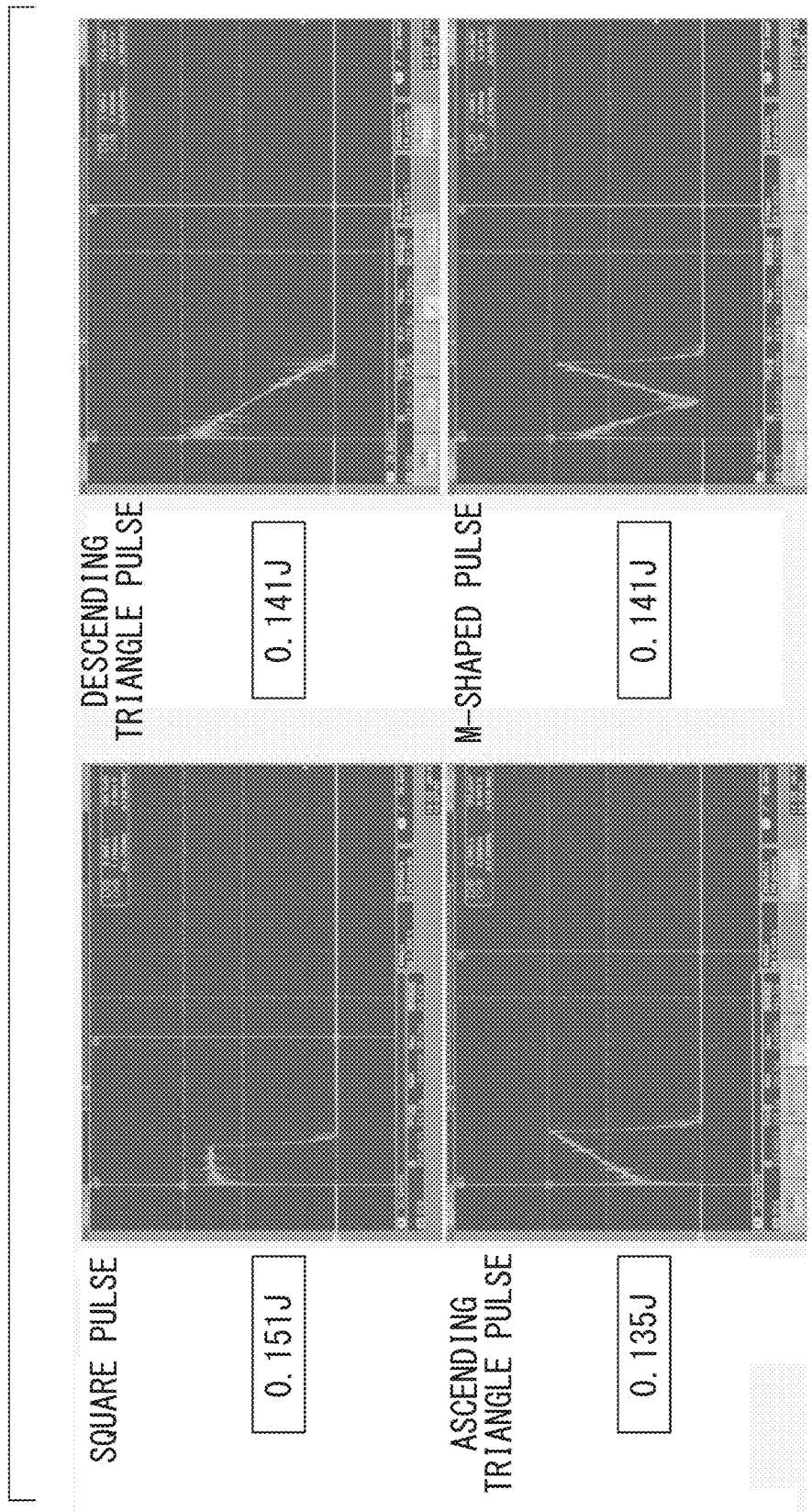
FIG. 12 is a view showing an example of respective pulse shapes and pulse energy.

FIG. 12 shows a pulse shape and a pulse energy of each pulse.

For a laser apparatus 51, a thulium fiber laser (TLR-50/500-QCW-AC-Y16, IPG Photonics) was used. The pulse shape was generated by a function generator (WF1974, NF) 53.

Bubble Observation

Figure 13:
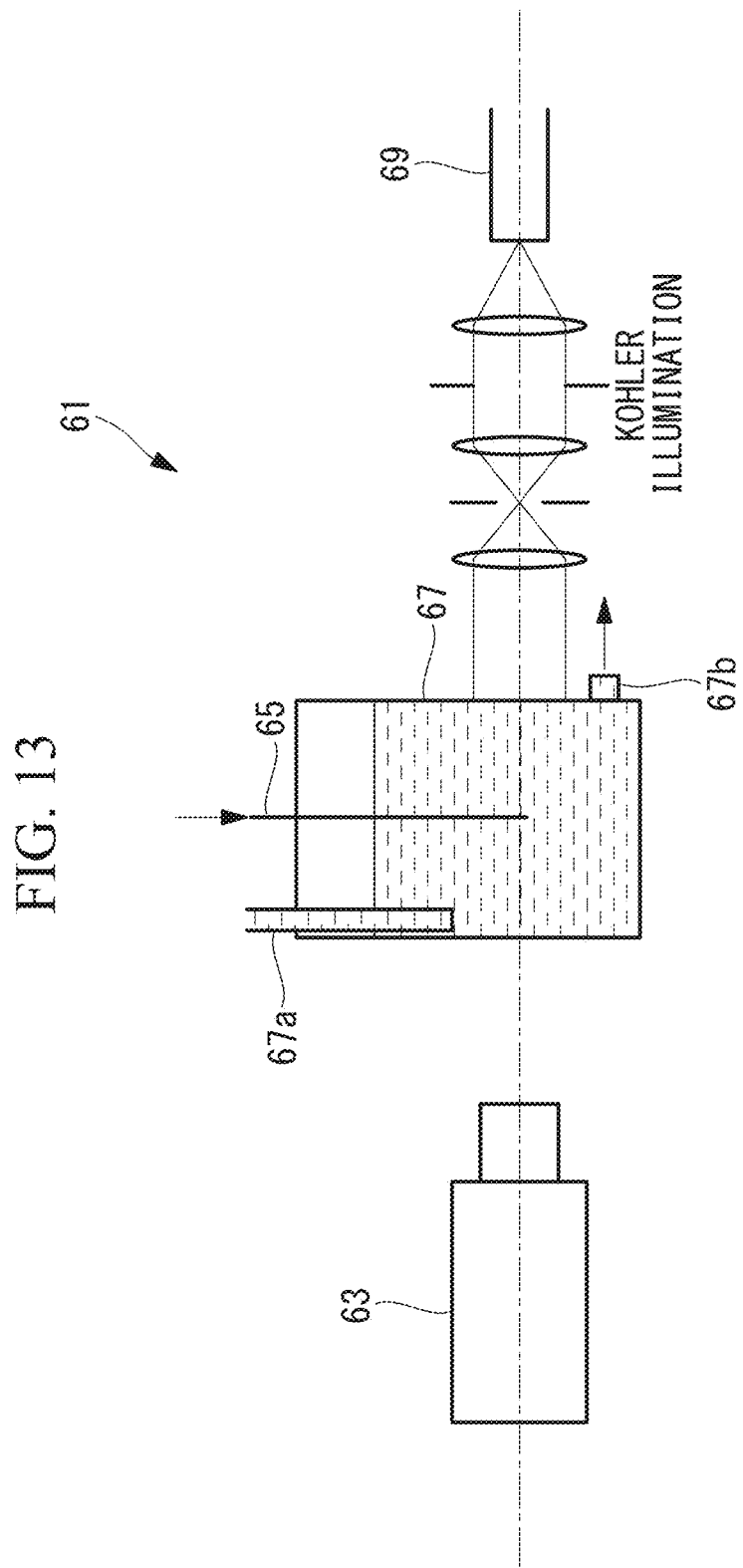
FIG. 13 is a view showing an example of a bubble shape analysis system.

As shown in FIG. 13, a bubble formation process of each pulse was photographed and recorded using a high-speed digital camera (Fastcam SA-Z, Photoron) 63. A photographing speed was 100,000 frames/sec.

FIG. 13 shows a setup of a bubble shape analysis system 61.

From a back surface of an acrylic case 67 in which an optical fiber 65 was installed, a photographing region was illuminated by a Kohler illumination using a halogen lamp as a light source 69. Bubbles appear as shadows in images taken by the camera. Reference numeral 67a indicates an irrigation inlet, and reference numeral 67b indicates an irrigation outlet.

Figure 14:
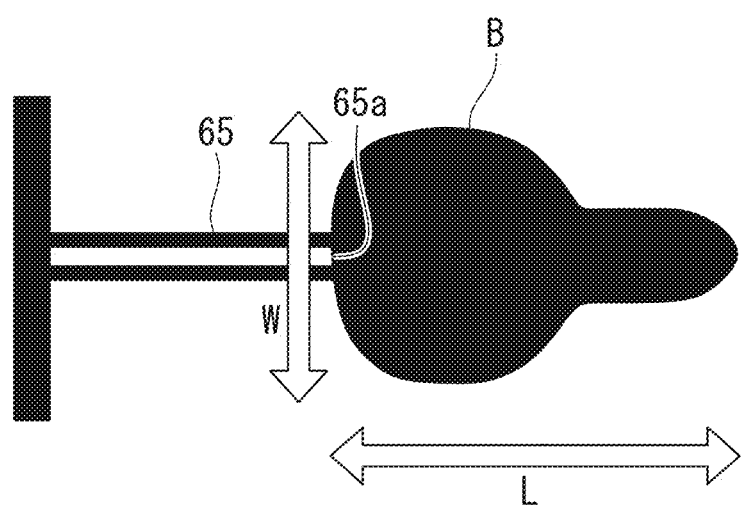
FIG. 14 is a view illustrating a bubble length and a bubble width.

As shown in FIG. 14, a bubble length (L) was defined as a maximum length of the bubble B continuous from a fiber end 65a, and a bubble width (W) was defined as a maximum value of the bubble width in a direction orthogonal to the optical fiber 65.

Figure 15:
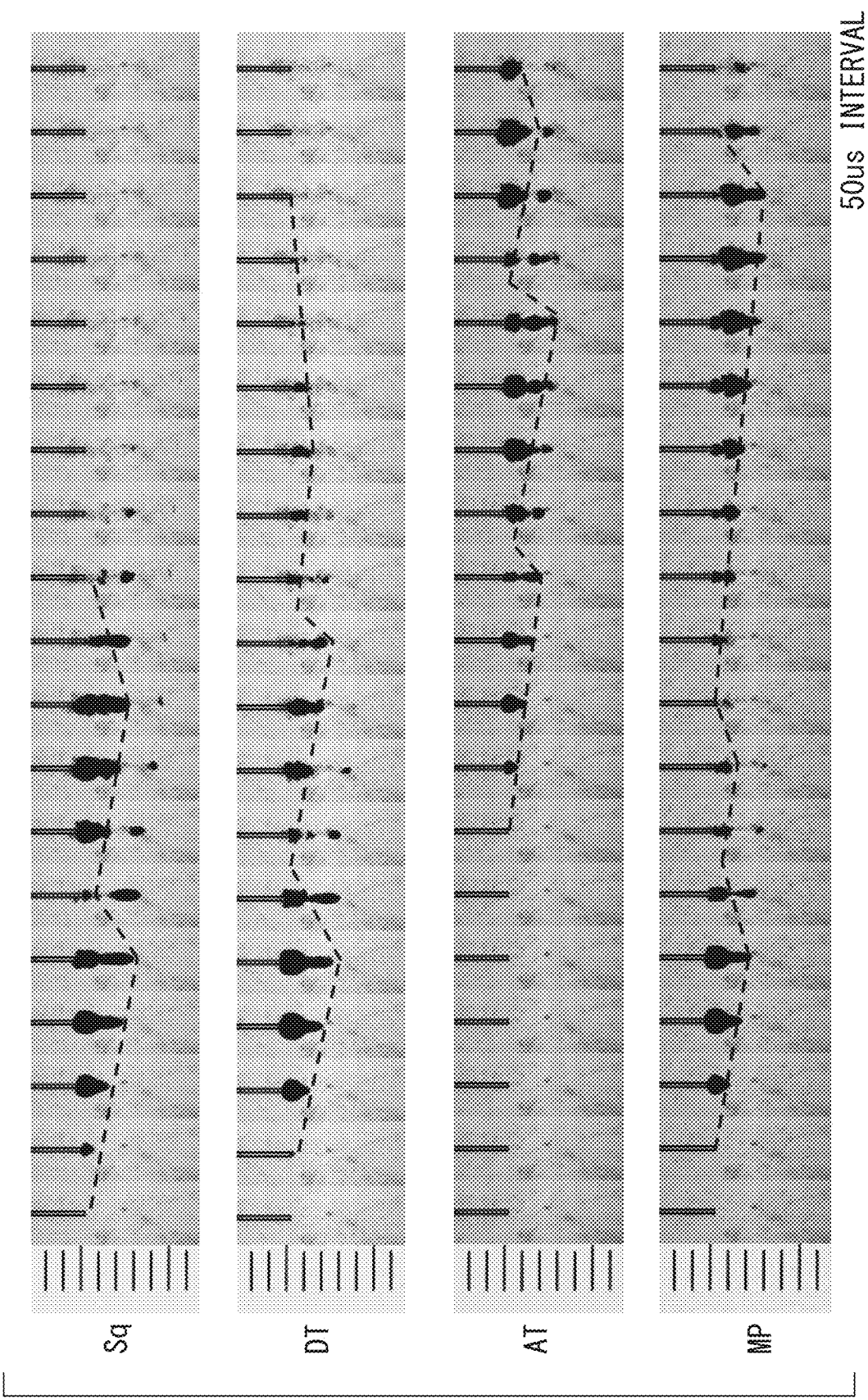
FIG. 15 is a view illustrating a bubble formation process of each pulse.

FIG. 15 shows a bubble formation process of each pulse.

In a case of a square pulse, two bubbles B were continuously generated and disappeared from the fiber end 65a. Lengths of the two bubbles were similar. In a case of a descending triangle pulse, three bubbles B were continuously generated and disappeared from the fiber end 65a. Lengths of the three bubbles gradually became shorter.

In an ascending triangle pulse, three bubbles B were continuously generated and disappeared from the fiber end 65a, and lengths of the three bubbles gradually became longer. In an M-shaped pulse, three bubbles B were continuously generated and disappeared from the fiber end 65a. Length of the first bubble B was similar to that of the third bubble B, and length of the second was shorter than those of the first and third bubbles.

Figure 16:
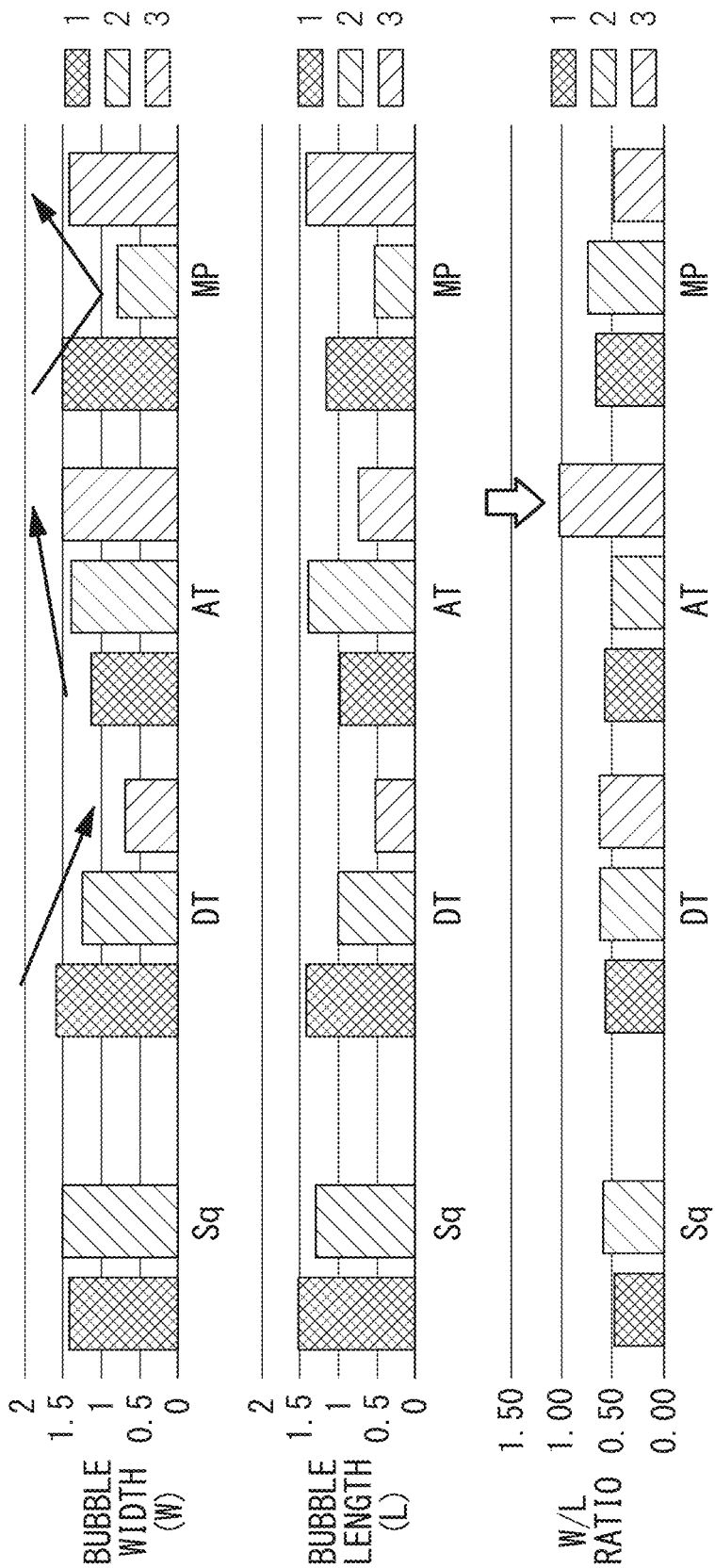
FIG. 16 is a view illustrating a bubble width, a bubble length, and a ratio of the bubble width to the bubble length for each pulse shape.

FIG. 16 shows a width, a length, and a ratio of the width to the length of each of a plurality of bubbles B that are continuously generated and disappeared in each pulse shape.

A size sequence of the plurality of bubble widths in each pulse shape differs depending on the pulse shape. All the bubbles B of the pulse shape showed a long elliptical shape in a longitudinal axis direction of the optical fiber 65, but the shape of the third bubble B of the ascending triangle pulse was close to spherical.

Suction Effect and Stone Retropulsion

Figure 17A:
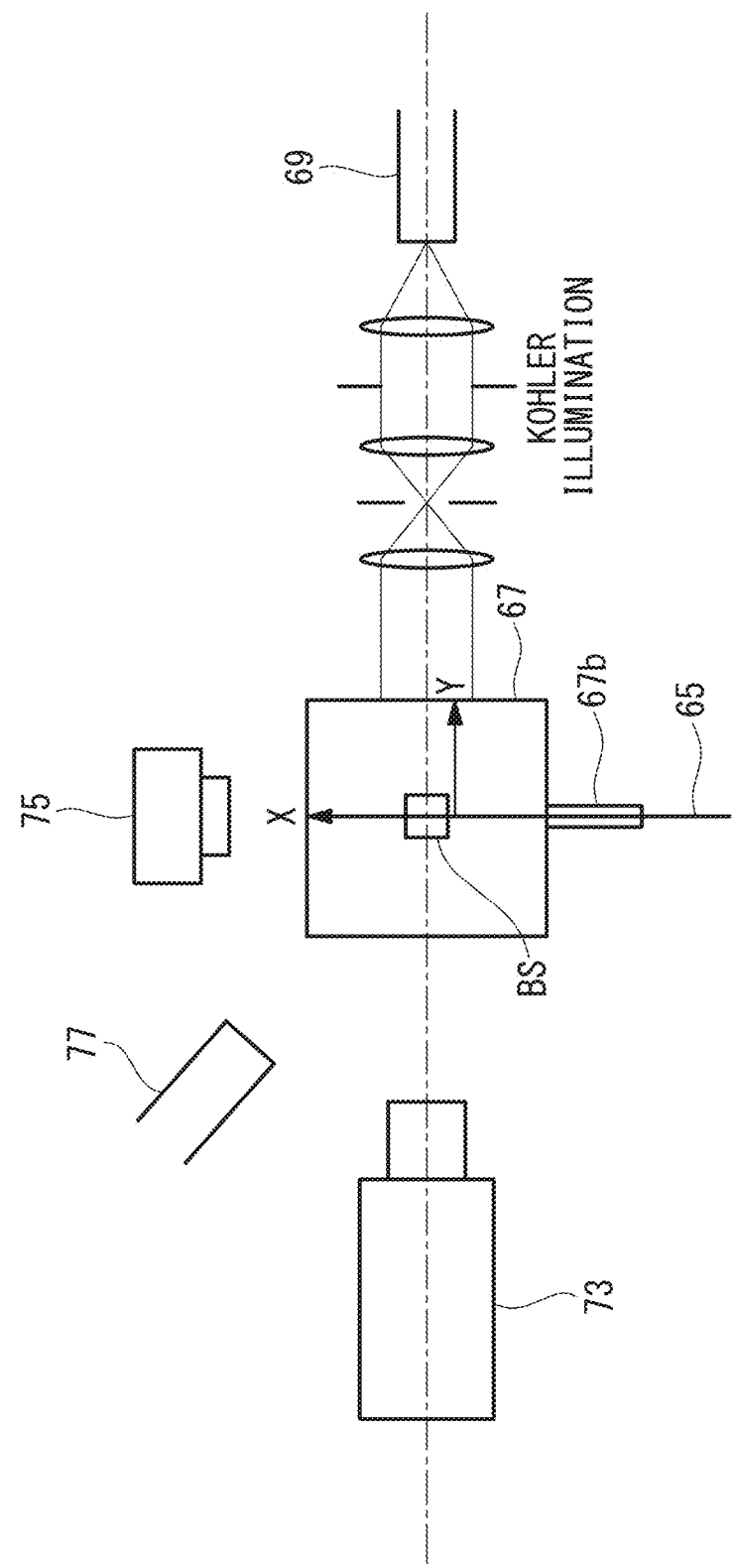
FIG. 17A is a view showing an example of an experimental system that evaluates a suction effect in a frontal direction of a fiber.
Figure 17B:
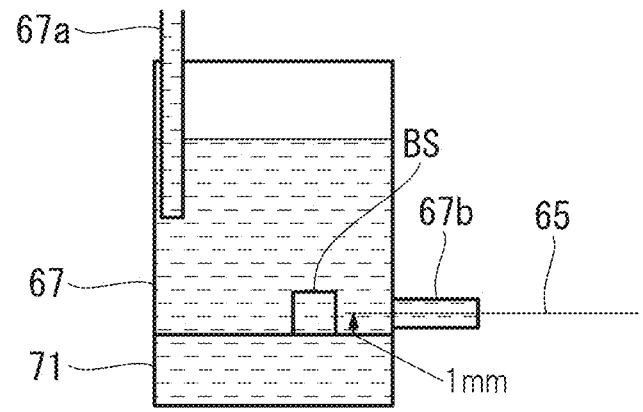
FIG. 17B is a view of surroundings of a stone phantom shown in FIG. 17A as viewed from a side.

FIGS. 17A and 17B show an experimental system for evaluating a suction effect in a frontal direction of the fiber.

A 2 mm-square stone phantom (BegoStone plus, compounding ratio 5:1, Bego Canada) BS is placed on a polystyrene (PS) cell 71. The optical fiber 65 is installed in a horizontal direction at a height of 1 mm from an upper surface of the PS cell 71.

The optical fiber 65 and the stone phantom BS are photographed from the side by a video camera (ARTCAM-130MI-BW, ARTRAY) 73. In order to evaluate the magnitude of movement of the stone phantom BS, a digital camera 75 was installed above the stone phantom BS, and positions (X, Y) of the stone phantom BS before and after laser irradiation were acquired. Reference numeral 77 indicates a xenon lamp.

Figure 18:
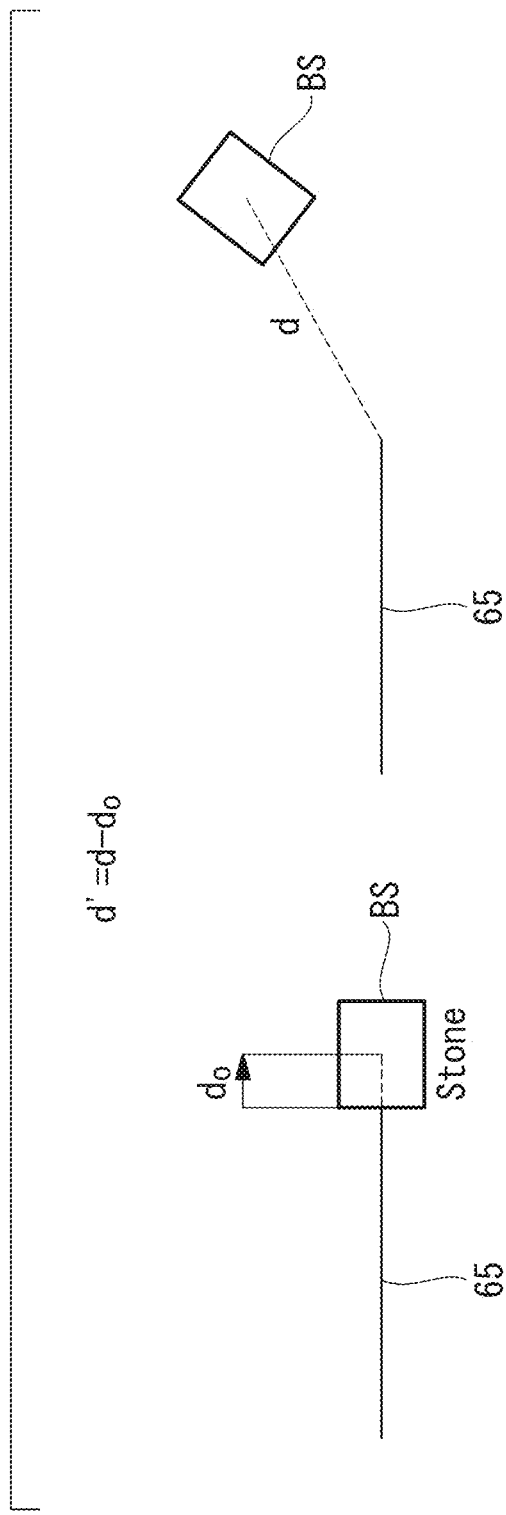
FIG. 18 is a view illustrating a stone retropulsion distance.

As shown in FIG. 18, a stone retropulsion distance was a numerical value (d') obtained by subtracting, as an offset, a half-value width ($d_0$) of the stone phantom BS from a distance between a tip of the optical fiber 65 after the end of laser irradiation and the center of gravity of the stone phantom BS.

A 2 mm-square stone phantom BS when the distance between the tip of the optical fiber 65 and the stone phantom BS is 0 mm and 0.5 mm and a 5 mm-square stone phantom BS when such a distance is 0 mm were irradiated with lasers of respective pulse shapes. Under each condition, N=3. N indicates the number of trials of each experiment.

Figure 19:
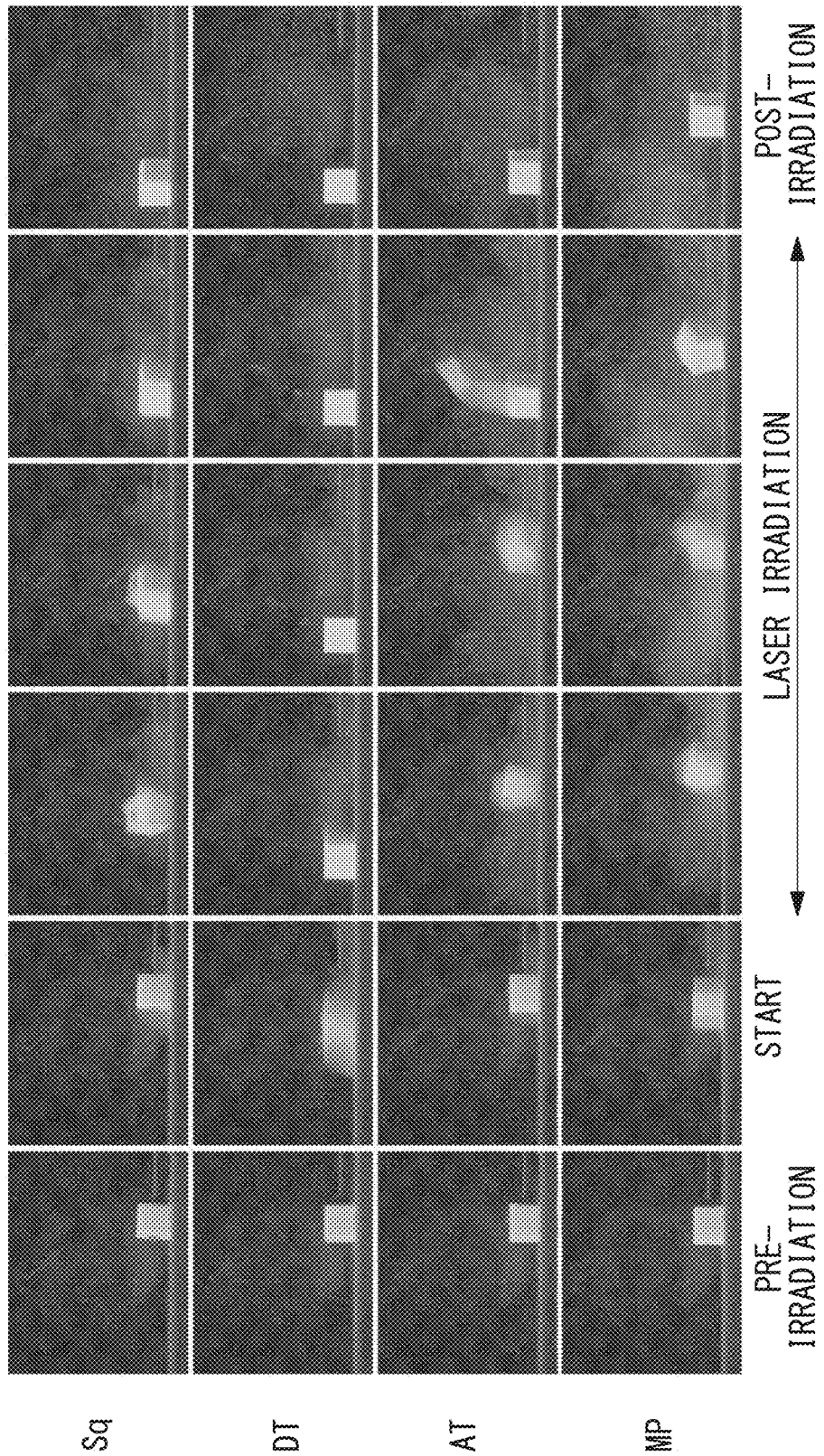
FIG. 19 is a view illustrating an example of an analysis result of behavior of a 2 mm-square stone phantom in each pulse shape.

FIG. 19 shows an example of analysis results of behavior of the stone phantom BS in the respective pulse shape when the distance between the tip of the optical fiber 65 and the 2 mm-square stone phantom BS is 0.5 mm.

In the square pulse and the descending triangle pulse, the stone phantom BS slid in one direction and stopped immediately after the start of laser irradiation. In the ascending triangle pulse and the M-shaped pulse, a phenomenon (suction effect) was observed in which the stone phantom BS was once apart from the optical fiber 65 and then approached or rotated on the spot during laser irradiation.

In the ascending triangle pulse, the stone phantom BS attracted to the tip of the optical fiber 65 immediately before the end of laser irradiation was blown off in a large arc. As a result, the position of the stone phantom BS immediately after the end of laser irradiation is not much different compared with the cases of the square pulse and the ascending triangle pulse. In the case of the M-shaped pulse, the position of the stone phantom BS immediately after the end of laser irradiation is closer to the tip of the optical fiber 65 compared with other examples.

Figure 20:
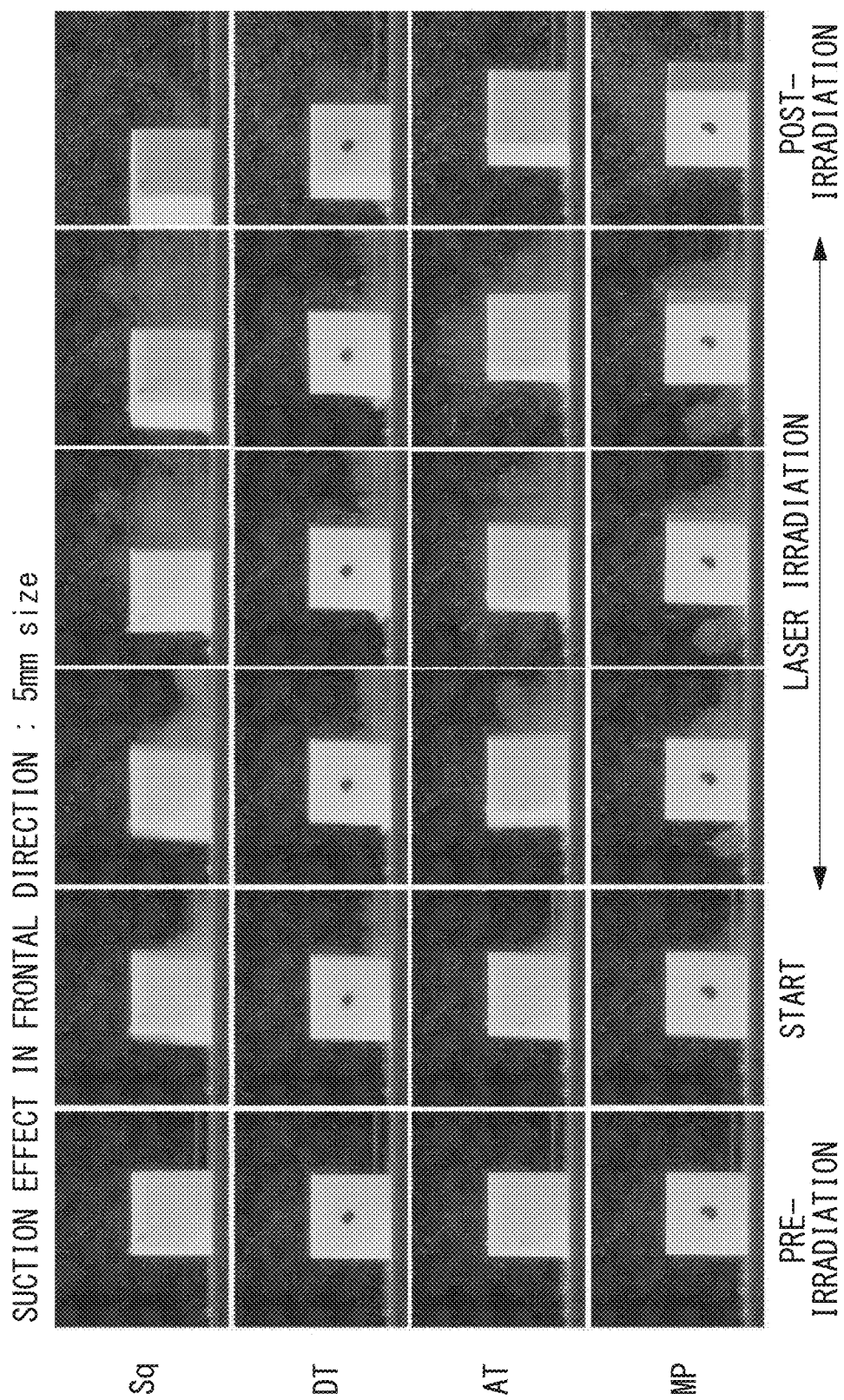
FIG. 20 is a view illustrating an example of an analysis result of behavior of a 5 mm-square stone phantom in each pulse shape.

FIG. 20 shows an example of results in the 5 mm-square stone phantom BS when the distance between the tip of the optical fiber 65 and the stone phantom BS is 0 mm.

In the square pulse, the suction effect was weak against the stone phantom BS, but the stone phantom BS slid greatly. In the descending triangle pulse, the stone phantom BS slid in one direction after laser irradiation and then stopped. In the ascending triangle pulse and the M-shaped pulse, a suction effect phenomenon was shown during laser irradiation, and the stone phantom BS stopped at a position close to the tip of the optical fiber 65 after the end of laser irradiation.

As a result of the above-described moving image analysis, a case where the suction effect phenomenon is recognized was regarded as suction success, a case where the suction effect phenomenon is not recognized was regarded as suction failure, and Table 2 summarized the number of times of suction success out of trials of N=3 under each condition, as suction success rate.

TABLE 2

| | Suction Success Rate | | |
|---|---|---|---|
| | Size, mm | 2 | 2 | 5 |
| | Distance, mm | 0 | 0.5 | 0 |
| 1 | Sq | 1/3 | 1/3 | 1/3 |
| 2 | DT | 0/3 | 0/3 | 0/3 |
| 3 | AT | 1/3 | 3/3 | 3/3 |
| 4 | MP | 0/3 | 3/3 | 3/3 |

In the ascending triangle pulse and the M-shaped pulse, the suction success rate was high in the case of the 2 mm-square stone phantom BS (the distance between the optical fiber and the stone phantom: 0.5 mm) and in the case of the 5 mm-square stone phantom BS. However, the suction success rate was low in the 2 mm-square stone phantom BS (the distance between the optical fiber and the stone phantom: 0 mm).

Table 3 indicates measurement results of a stone retropulsion distance.

TABLE 3

| | Stone Retropusion | | |
|---|---|---|---|
| | Size, mm | 2 | 2 | 5 |
| | Distance, mm | 0 | 0.5 | 0 |
| 1 | Sq | 9.3 ± 2.1 | 3.9 ± 3.5 | 1.8 ± 2.1 |
| 2 | DT | 9.6 ± 0.4 | 6.0 ± 1.0 | 2.2 ± 0.2 |
| 3 | AT | 9.3 ± 0.7 | 8.0 ± 1.6 | 0.7 ± 0.9 |
| 4 | MP | 6.0 ± 0.5 | 2.3 ± 2.0 | 0.5 ± 0.3 |

The M-shaped pulse had a smaller stone retropulsion distance than those of the other pulse shapes under any condition. The ascending triangle pulse had a small stone retropulsion distance under the condition of the 5 mm-square stone phantom BS, and was comparable to the other pulse shapes under other conditions.

Figure 21:
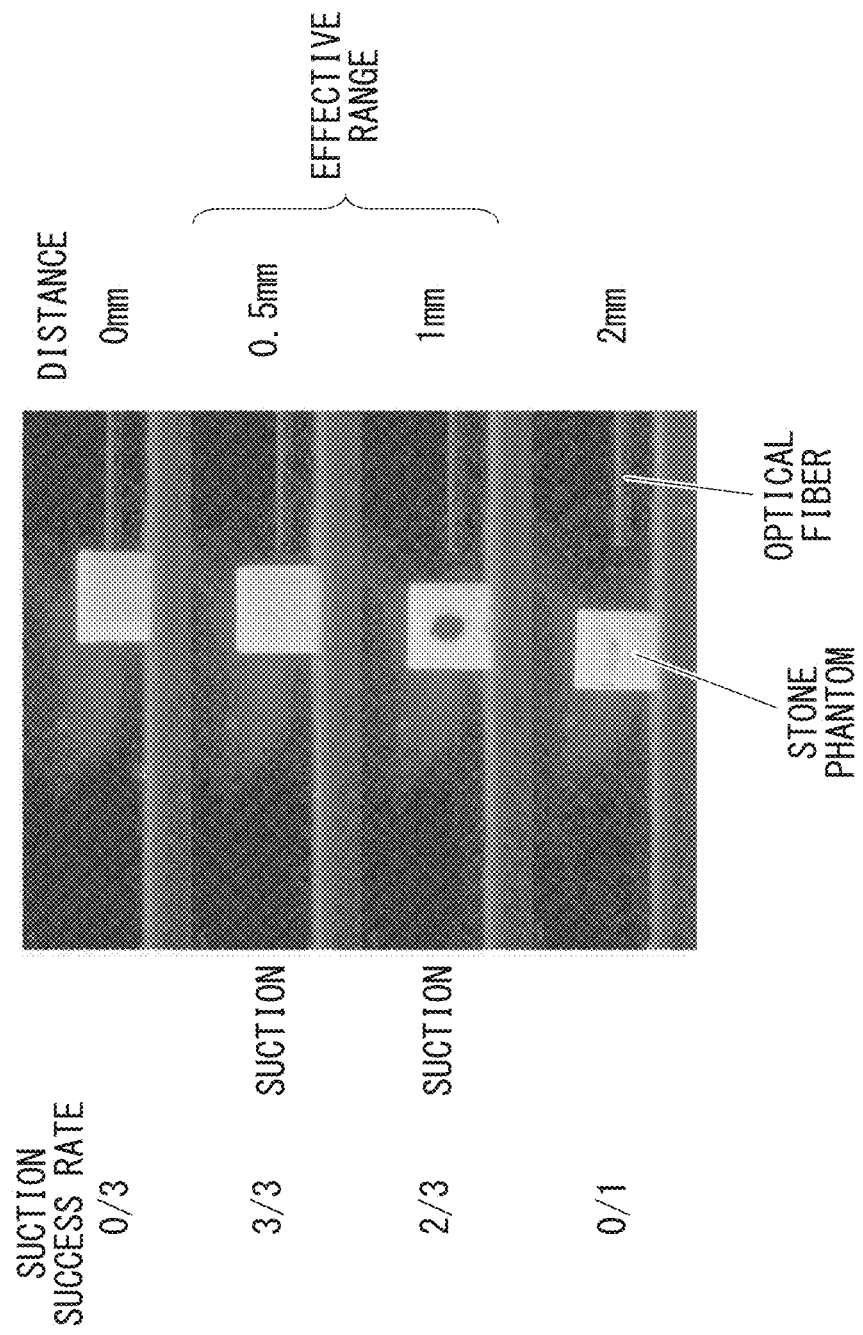
FIG. 21 is a view illustrating a relation between a distance from a fiber end to a stone phantom and a suction success rate.

As shown in FIG. 21, in order to evaluate a relation between the distance from the optical fiber 65 to the stone phantom BS and the suction success rate, moving image analysis was performed on the behavior of the stone phantom BS at N=3 under conditions that the distance between the tip of the optical fiber 65 and the stone phantom BS were 0 mm, 0.5 mm, 1 mm, and 2 mm. The ascending triangle pulse was used as a pulse shape in this experiment. As a result, the suction success rate was high under the conditions that the distance was 0.5 mm and 1 mm. In this way, it was confirmed that there is a separation distance at which the suction success rate increases.

As can be seen from the examination results of FIGS. 20 and 21, since the suction success rate may differ depending on conditions such as the distance between the target stone and the laser emission end and the size of the stone, it is preferable to carry out the lithotripsy while grasping these conditions. As an image acquisition means for that purpose, it is preferable to have a focal length capable of imaging a range in which the distance from the tip (laser emission end) of the optical fiber 65 to the stone phantom BS is 0.5 mm, 1 mm, and 2 mm.

Figure 22:
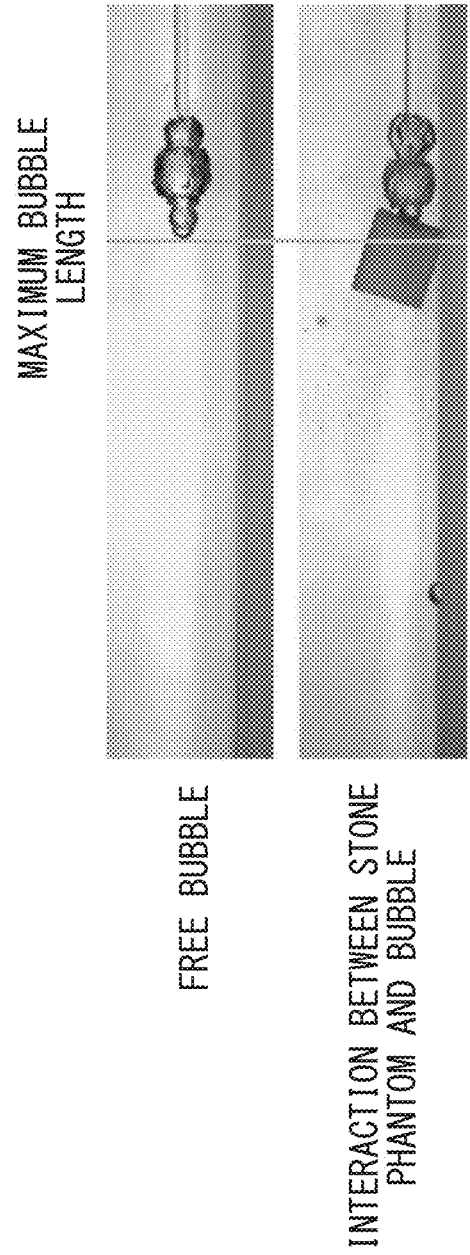
FIG. 22 is a view illustrating a trapped position and a bubble length of a stone phantom.

Using the high-speed digital camera (Fastcam SA-Z, Photoron) 63, the bubble B was observed and an interaction between the optical fiber 65 and the stone phantom BS was measured at a photographing speed of 50,000 frames/sec, as shown in FIG. 22. As a result, in the example where the suction effect was successful, it was found that the bubble B pulls in and traps the stone phantom BS below the maximum length of the bubble B.

Detailed Mechanism of Suction Effect

Figure 23:
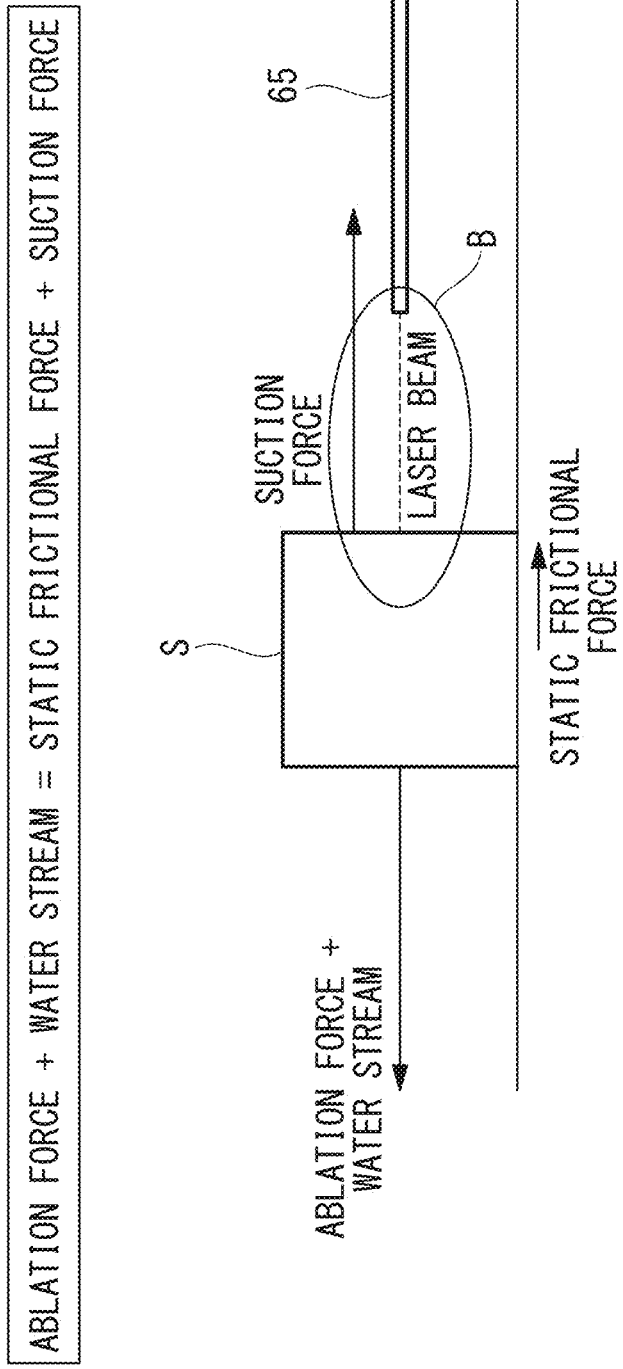
FIG. 23 is a view illustrating a stone and forces interacting with a bubble.

In the behavior of the stone S interacting with the bubble B, as shown in FIG. 23, a relation between four forces is important, the four forces including a momentary attractive force accompanying the contraction of the bubble B, a jet water stream generated after the collapse of the bubble B, an ablation force generated when the stone S is crushed by the irradiated laser beam passing through the bubble B and hitting the stone S, and a static frictional force with the ground acting on the stone S.

The bubble B is generated by optical energy of the irradiated laser beam being absorbed by the water. Then, when the expanded bubble B comes into contact with the stone S, the stone S is crushed by the optical energy that reaches the stone S through the bubble B. When the expanded bubble B turns to contraction, a suction force acts in a contraction direction of the bubble B due to a pressure difference between the inside and outside of the bubble B. Due to the reaction of the bubble B that collapses due to the contraction, the water stream is generated in a direction in which the stone S is pushed away.

When the sum of the ablation force and the water stream force exceeds the static frictional force acting on the stone S, the stone S moves backward. At this time, after the bubble B reaches the stone S, the irradiation energy is promptly reduced, whereby the ablation force is reduced. When the suction force accompanying the contraction of the bubble B exceeds the static frictional force acting on the stone S or an inertial force of the stone S and the water stream after the collapse of the bubble is lower than the inertial force of the stone S, a suction effect occurs.

Comparison with Conventional Pulse Shape

In the conventional pulse shape, a plurality of bubbles are not coupled because a peak value of a pulse output is continuous or a bubble generation period is short exclusively for obtaining a crushing effect, as in the case of the square shape or the stepped pulse. By a further study, the inventor assumes that, even in the case where the first and second pulses are used as disclosed in PTL 2, even when the bubble generated at the tip of the optical fiber reaches the stone by the interval, the bubble is then divided into the optical fiber side and the stone side, the remaining bubble attached to the stone side disappears at an arbitrary timing, and thus the retropulsion acts. In this way, since the concept of lithotripsy by the conventional pulse shape gives priority to injection of a large amount of energy into ablation of the stone S, even when there are conditions under which the suction effect occurs, it is considered the stone S is blown backward by the action of the retropulsion that exceeds the suction effect. In particular, regarding the square shape or the pulse with a sufficiently high output that produces only a crushing effect, since the generated bubble B is too small or the shape of the bubble is not coupled longitudinally in the laser irradiation direction, the retropulsion is superior even when the suction force occurs, and thus the inventor found by the study that the suction effect is difficult to be exerted.

The ascending triangle and the M-shaped pulse have an effect of attracting the stone S under appropriate distance conditions. Further, the M-shaped pulse has small retropulsion of the stone.

Method: Suction Effect on Fiber Side

Figure 24:
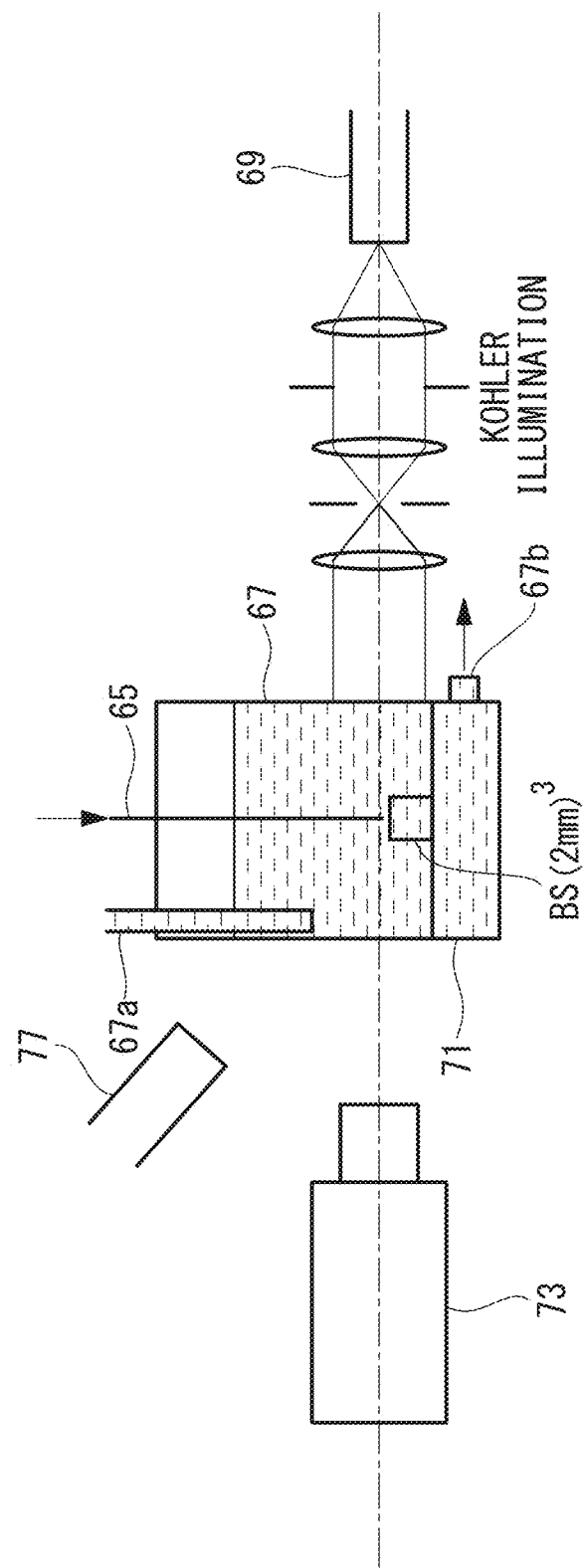
FIG. 24 is a view showing an experimental system that evaluates a suction effect on a fiber side.

As shown in FIG. 24, a PS cell 71 was laid in an acrylic case 67, and a 2 mm-square stone phantom (begostone) BS was placed on the PS cell 71. A saline solution was injected from an irrigation inlet 67a at a rate of about 20 ml/min, and the saline solution was discharged from an irrigation outlet 67b. Movement of a stone phantom BS was photographed using a high-speed digital camera (Fastcam SA-Z, Photoron) 63, and illumination was performed with a xenon light source 77. In the acrylic case 67, an optical fiber 65 with a core diameter of 200 um was disposed perpendicular to an upper surface of the PS cell 71.

Figure 25:
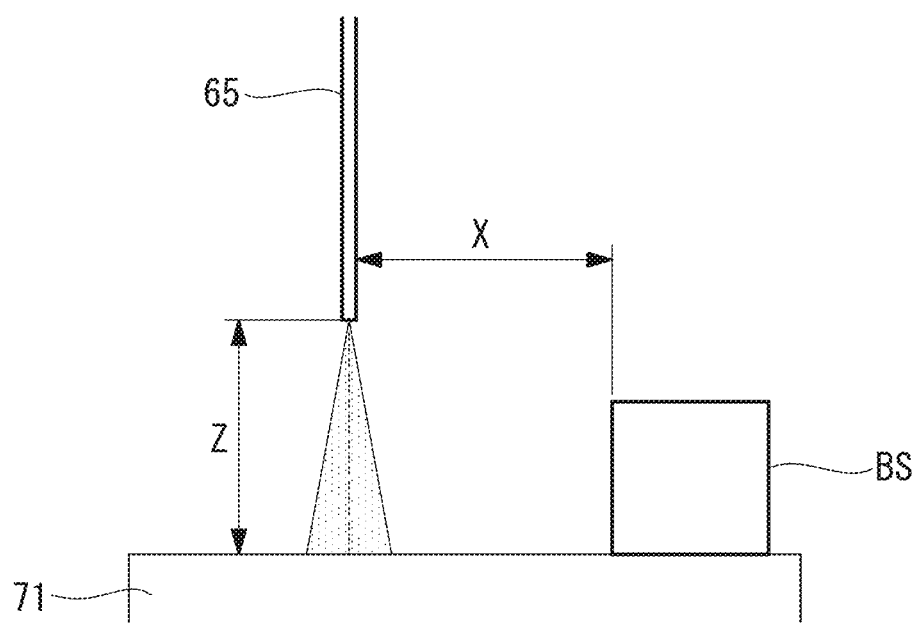
FIG. 25 is a view illustrating a distance between a fiber and a stone phantom.

As shown in FIG. 25, a distance between the optical fiber 65 and the stone phantom BS was adjusted as X, and a distance from the upper surface of the PS cell 71 to the tip of the optical fiber 65 was adjusted as Z.

Result: Suction Effect on Fiber Side

Figure 26:
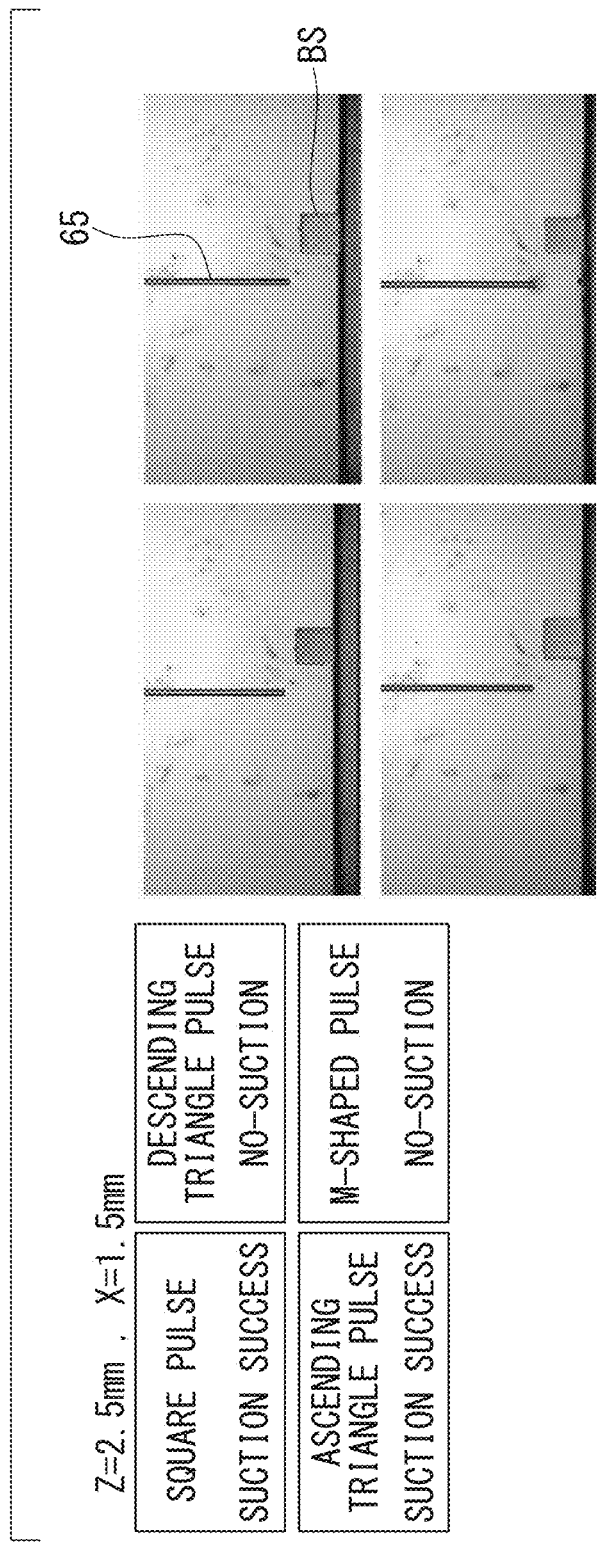
FIG. 26 is a view illustrating a suction effect on a fiber side for each pulse shape.

FIG. 26 shows evaluation result of suction effects of a square pulse, a descending triangle pulse, an ascending triangle pulse, and a M-shaped pulse under arrangement conditions of Z=2.5 mm and X=1.5 mm. Irradiation conditions of the laser beam were a pulse energy of 0.2 J, a pulse frequency of 80 Hz, and a laser irradiation time of 1 second.

Among these pulses, in the square pulse and the ascending triangle pulse, the stone phantom BS was attracted to the bottom of the optical fiber 65, so that the stone phantom BS was irradiated with the laser beam, and as a result, dust was raised. This was defined as suction success, and the presence or absence of the suction success was determined by analysis of each of the acquired moving image data.

A suction velocity (Velocity) was calculated as a ratio of the distance (X) between the optical fiber 65 and the stone phantom BS in the case of the suction success to a time from a laser irradiation start (laser start) until the laser beam first hits the stone phantom BS (stone hit), that is, a time until the laser beam reaches the stone phantom BS earliest.

$$\text{Velocity(mm/sec)} = X/(t[\text{stone } hit] - t[\text{laser start}])$$

FIG. 27 shows results of the suction success rate and the suction velocity. The suction effect on the fiber side appeared more frequently in the case of the square pulse and the ascending triangle pulse. The suction velocity was reduced as the distance became longer. The square pulse has a stronger suction force than the ascending triangle pulse.

The suction effect on the fiber side is useful for accelerating the start of popcorn lithotripsy and for attracting one or more stones B located near the surroundings to the front of the fiber. From the results of this experiment, the suction effect on the fiber side appeared in the square pulse and the ascending triangle pulse, and the square pulse had a higher lateral suction force than the ascending triangle pulse.

However, since the square pulse has a higher energy delivery rate to the front of the fiber than the ascending triangle pulse, clinically, the remaining energy of the energy absorbed by water should be carefully delivered to the biological mucosa such that a temperature of the biological mucosa does not rise above a normal state. In this regard, it is considered that the stepped pulse should be also carefully treated as well. On the other hand, regarding the ascending triangle pulse, since the peak value pulse is only a moment, the energy delivered to the front of the fiber is small and the suction effect on the fiber side is obtained, whereby the risk of damage to the biological mucosa can be reduced and the stone S on the fiber side can be pulled in the optical fiber 65. In this regard, since it is considered that the M-shaped pulse also causes less damage to the living body, as in a modification to be described below, it is preferable to change the gradient of the output every period constituting the pulse such that the shape of the M-shaped pulse approaches the shape of the ascending triangle. As described above, it is considered that the pulse shape of the present invention is more suitable than the square pulse for the laser lithotripsy used in the living body in terms of the lateral suction effect.

Modification of Pulse Shape

Figure 28:
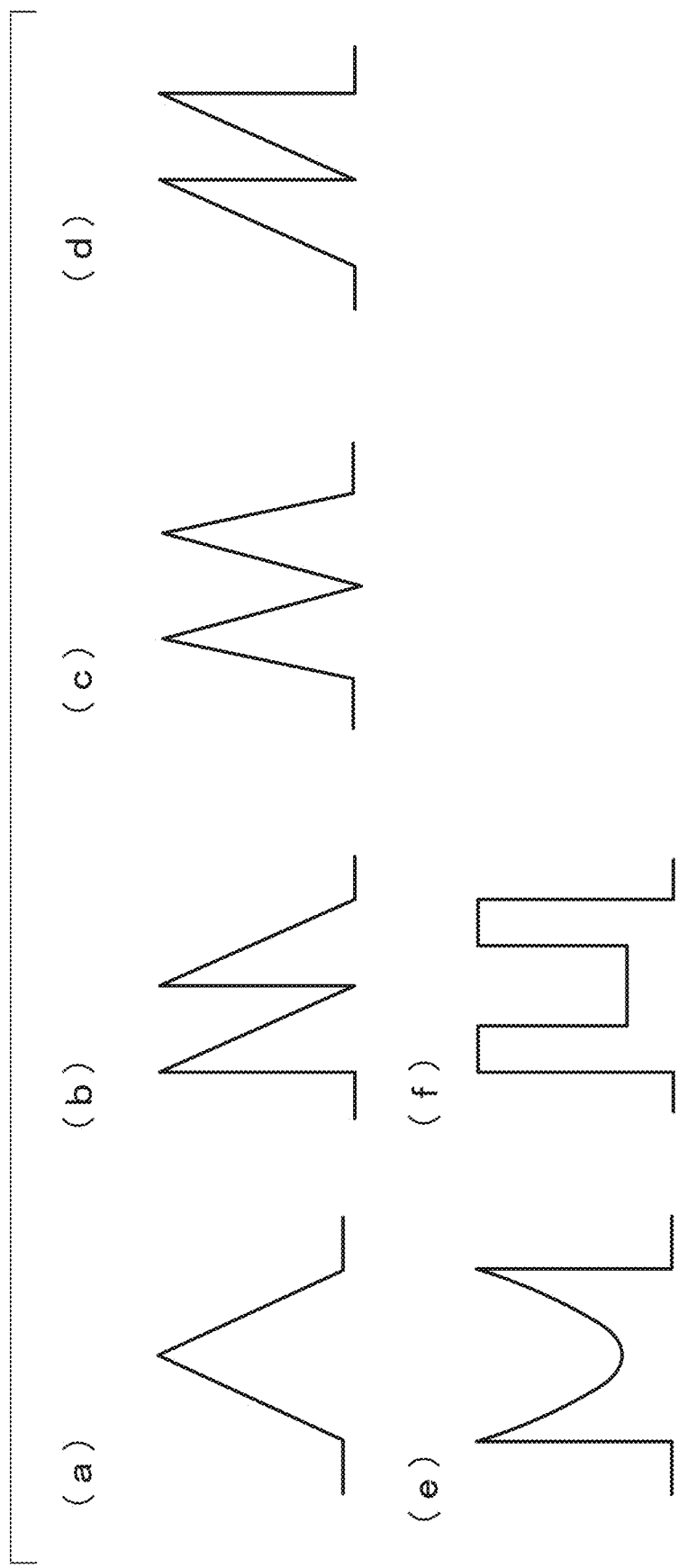
FIG. 28 is a view showing an example of a pulse shape.
Figure 29:
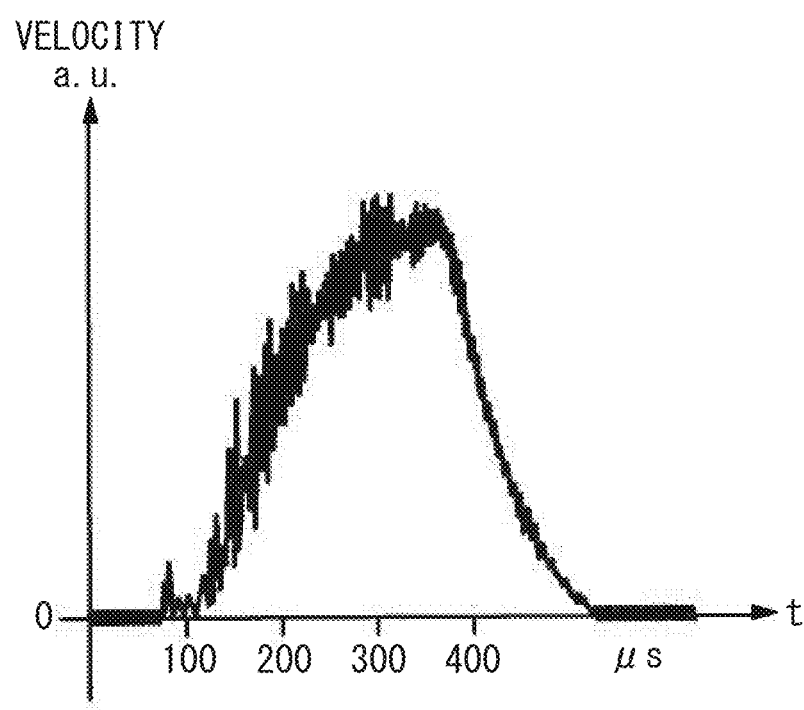
FIG. 29 is a view illustrating PTL 1.
Figure 30:
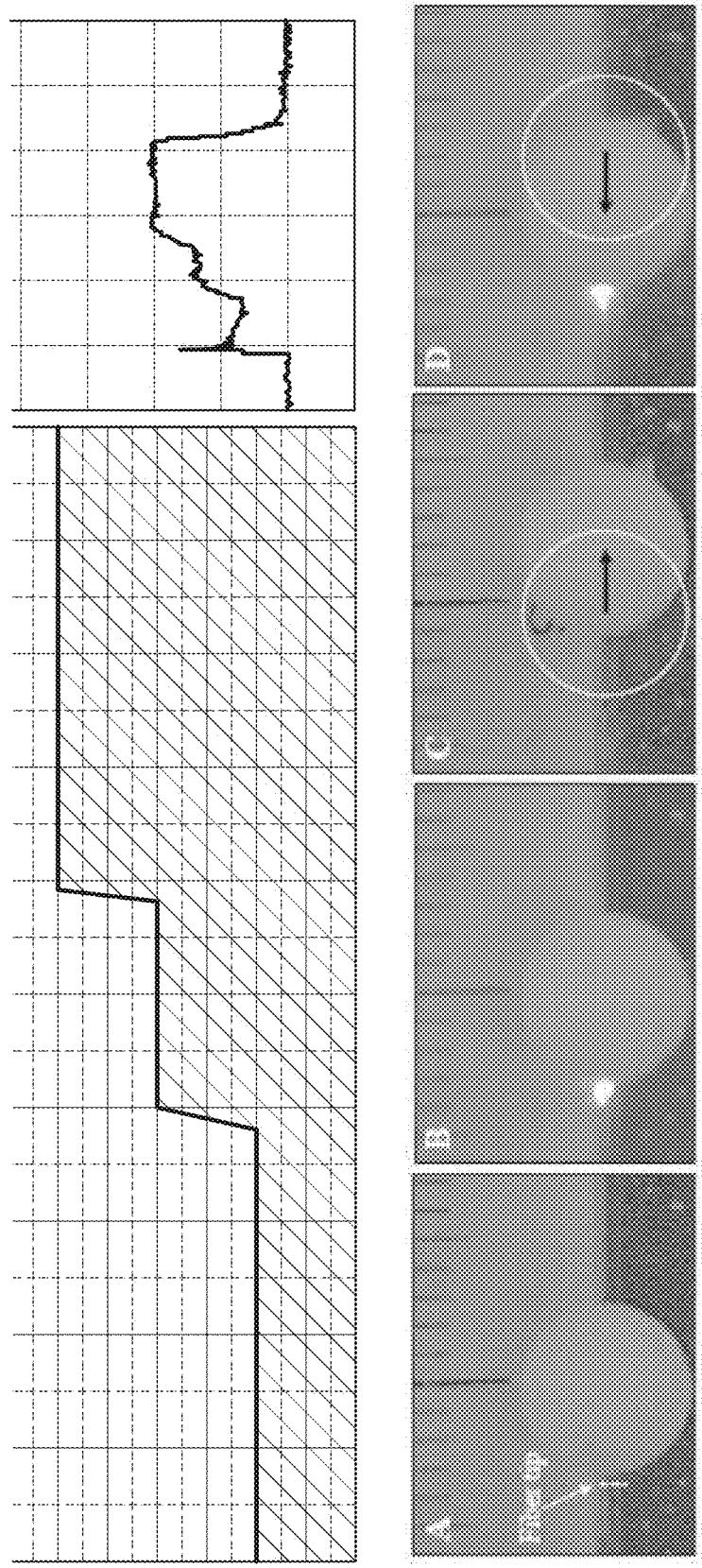
FIG. 30 is a view illustrating NPL 1.

Even when the pulse shapes are pulse shapes shown in FIGS. 28(*a*) to 28(*f*), the same effect is exhibited. FIG. 28(*a*) shows a modification of the ascending triangle pulse, and FIGS. 28(*b*) to 28(*f*) show modifications of the M-shaped pulse. It is assumed that all of these modifications have the gradient of the pulse waveform as described above. According to the pulse shape shown in FIG. 28(*a*), as a modification of the ascending triangle pulse, the substantially same predetermined gradient may be provided for a first period in which the output monotonically increases and a second period in which the output monotonically decreases. Further, according to the pulse shapes shown in FIGS. 28(*b*) to 28(*d*), as a modification of the M-shaped pulse, the magnitude relation of a relative gradient between a first set of pulses corresponding to the first and fourth periods in which the pulse output monotonically increases and a second set of pulses corresponding to the second and third periods in which the pulse output monotonically decreases may be arbitrarily changed. In Example of the present invention, a polygonal line indicates a shape of a portion in which the pulse output changes from the increase to the decrease in the first period in which the output monotonically increases and the second period in which the output monotonically decreases, which enhances the disappearing action of the bubble, but it does not have to be in the shape of the polygonal line in other portions where the disappearing of the bubble is not expected. Therefore, for example, as in the pulse shape shown in FIG. 28(*e*), a shape of a portion in which the pulse output changes from the decrease to the increase between the third period corresponding to the central portion of the M-shaped pulse and the first period may be changed to a curve having an inflection point. Further, according to Example of the present invention, as shown in FIG. 10, it is possible to promptly proceed with the next bubble generation with respect to the solution W warmed in the third period by making the pulse output of the central portion of the M-shaped pulse larger than zero. Therefore, as shown in FIGS. 28(*e*) and 28(*f*), the pulse shape may be a curve or a square shape forming a valley. Further, according to FIG. 28(*f*), it is possible to change each of portions of two peak values into a square shape having a narrow width, only in the modification of the M-shaped pulse. In other words, the bubbles coupled in a sufficiently warmed liquid at the central portion of the M-shaped pulse may be difficult to be uncoupled with the square pulse with a width of at most less than 30% of the total as shown in the drawing.

As described above, according to Example, the pulse shape of the laser beam is adjusted, and thus the force becomes effective that the contraction of the bubble B generated in the liquid attracts the stone B. Thereby, the ablation force caused by the lithotripsy is reduced, so the stone retropulsion is reduced or the damage to the biological mucosa is minimized. In particular, when one or more stones S are attracted to the irradiation region of the laser beam, the user can move the laser irradiation apparatus to reduce the trouble of accurately aiming each stone S, which contributes to treatment in a short time.

Further, when the laser beam is irradiated between two or more stones S, these stones S are collected in the irradiation region of the laser beam, and then each of the stone S can be crushed at the same time. When a plurality of stone S are crushed at the same time, it is possible to reduce the temperature rise in the body. Further, one or more stones S attracted to the laser irradiation region may stay in the irradiation region until the stones are crushed to a size that can be naturally discharged from the body.

Although the embodiment of the present invention has been described in detail with reference to the drawings, the specific configuration is not limited to such an embodiment, and includes design changes within a range that does not deviate from the scope of the present invention. For example, the present invention is not limited to the embodiment and the modification described above, and may be embodiments in which these embodiments and the modification are appropriately combined without being limited particularly. The present invention is applicable to various types of endoscopes other than a ureteroscope, such as a urethroscope, a cystoscope, a cholangioscope, a hysteroscope, a duodenum endoscope or a digestive tract endoscope.

The following aspects can be also derived from the embodiments.

A first aspect of the present invention provides a laser lithotripsy apparatus including a pulse generation unit that pulses a laser beam oscillated from a laser beam source; an output adjustment unit that adjusts an output of the laser beam pulsed by the pulse generation unit; and a laser emission end that emits the laser beam adjusted in the output by the output adjustment unit, to a stone in a liquid, wherein the output adjustment unit switches the output of the laser beam to a second period in which the output monotonically decreases with a gradient larger than a predetermined gradient, after a first period in which the output monotonically increases.

According to the above aspect, the laser beam pulsed by the pulse generation unit is emitted from the laser emission end, and the stone in the liquid is irradiated with the laser beam, whereby the stone is crushed. The laser beam reaches the stone by passing through the bubble generated in the liquid by the laser beam.

In the case, after the output of the pulse-like laser beam monotonically increases in the first period, the output is monotonically decreased with the gradient larger than the predetermined gradient in the second period by the output adjustment unit. After the plurality of bubbles are generated continuously from the laser emission end by the laser beam emitted in the first period, the plurality of bubbles are bound, and thus the bubble binding body is formed. The laser beam the output of which is reduced in the second period turns around and suddenly loses the bubble generating force, so that the bubble binding body disappears almost at the same time. Thereby, a suction force can be generated, and the stone can be attracted toward the laser emission end in a frontal direction. Note that the bubble binding body may or may not come into contact with the stone before it disappears. In the case where the bubble binding body comes into contact with the stone before it disappears, it is preferable to cause the bubble binding body to disappear at the moment when the bubble binding body comes into contact with the stone.

Therefore, the stone can be irradiated with the laser beam within a certain distance from the fiber emission end without moving the stone in a direction away from the fiber emission end due to the impact of the laser beam. Accordingly, the suction effect can be effectively used, and the stone can be efficiently irradiated with the laser beam.

In the laser lithotripsy apparatus according to the aspect described above, the laser lithotripsy apparatus may further include an optical fiber having the laser emission end.

With such a configuration, the optical fiber is inserted into the body, and thus the laser emission end can be disposed to be face the stone.

In the laser lithotripsy apparatus according to the aspect described above, the optical fiber may be added with thulium.

A second aspect of the present invention provides a laser lithotripsy system including: a pulse generation unit that pulses a laser beam oscillated from a laser beam source; an output adjustment unit that adjusts an output of the laser beam pulsed by the pulse generation unit; a laser emission end that emits the laser beam adjusted by the output adjustment unit to a stone in a liquid; an image acquisition unit that acquires an image on an optical path of the laser beam including the laser emission end and the stone; and a display unit that displays the image acquired by the image acquisition unit, wherein the output adjustment unit switches the output of the laser beam to a second period in which the output monotonically decreases with a gradient larger than a predetermined gradient, after a first period in which the output monotonically increases, and the display unit displays the image showing the stone and behavior of a bubble generated by the laser beam.

According to the present aspect, after the output of the pulse-like laser beam is monotonically increased in the first period, the output is monotonically decreased with the gradient larger than the predetermined gradient in the second period by the output adjustment unit. Further, the image on the optical path including the laser emission end and the stone acquired by the image acquisition unit is displayed by the display unit. When the display unit displays the image showing the stone and behavior of the bubble generated by the laser beam, the user can easily grasp the irradiation status of the stone with the laser beam.

In the laser lithotripsy system according to the aspect described above, the laser lithotripsy system may further include a calculation unit that calculates a distance between the laser emission end and the stone based on the image.

In the laser lithotripsy system according to the aspect described above, the display unit may display information regarding the distance.

With such a configuration, the user can easily grasp the distance between the laser emission end and the stone from image information displayed by the display unit and information regarding the distance.

A third aspect of the present invention provides a laser lithotripsy method of irradiating a stone in a liquid with a laser beam to crush the stone, the method including: emitting a pulse-like laser beam from a laser emission end disposed facing the stone to generate continuously a plurality of bubbles from the laser emission end; coupling the laser emission end and the stone by a bubble binding body formed by binding of the plurality of bubbles; and attracting the stone to the laser emission end by a suction force generated by disappearing of the bubble binding body.

According to the present aspect, when the laser beam is emitted from the laser emission end in the liquid, the plurality of bubbles are generated continuously from the laser emission end. Then, the laser emission end and the stone are coupled by the bubble binding body in which the plurality of bubbles are bound. Thereby, the laser beam passes through the bubble binding body, and thus the stone is irradiated with the laser beam. Then, the bubble binding body disappears, whereby the suction force is generated, and thus the stone is attracted to the laser emission end.

Therefore, the stone can be prevented from moving in the direction away from the laser emission end due to the impact of the laser beam, and the stone can be irradiated with the laser beam within a certain distance from the laser emission end. Therefore, the suction effect can be effectively used, and the stone can be efficiently irradiated with the laser beam.

In the laser lithotripsy method according to the aspect described above, the laser lithotripsy method may further include: switching an output of the laser beam to a second period in which the output monotonically decreases with a gradient larger than a predetermined gradient after a first period in which the output monotonically increases; generating the bubble binding body by the laser beam emitted in the first period; and causing the bubble binding body to disappear by the laser beam emitted in the second period.

After the output of the laser beam is monotonically increased in the first period, when the output of the laser beam is monotonically decreased with the gradient larger than the predetermined gradient in the second period, the plurality of bubbles coupled in the irradiation direction of the laser forcibly disappear almost at the same time to cause a large suction action, and thus the lithotripsy effectively using the suction effect can be realized.

In the laser lithotripsy method according to the aspect described above, the first period may be a period in which the output monotonically increases with a gradient smaller than the predetermined gradient.

With such a configuration, the plurality of bubbles are likely to be generated continuously from the laser emission end.

In the laser lithotripsy method according to the aspect described above, the laser lithotripsy method may further include switching the output of the laser beam to the first period after a third period in which the output monotonically decreases with a gradient smaller than the predetermined gradient.

The laser beam emitted in the third period easily reaches the stone without the bubble disappearing rapidly. Further, since the liquid on the optical path of the laser beam is warmed by the laser beam emitted in the third period before the laser beam is emitted in the first period, the bubble is easily generated by the laser beam emitted in the first period.

In the laser lithotripsy method according to the aspect described above, the laser lithotripsy method may further include switching the output of the laser beam to the third period after a fourth period in which the output monotonically increases with a gradient larger than the predetermined gradient.

The laser beam emitted in the fourth period can rapidly generate the bubble.

In the laser lithotripsy method according to the aspect described above, the gradient of the output of the laser beam may be in a range of 0.625 to 5.0 W/μs.

In the laser lithotripsy method according to the aspect described above, the gradient of the output of the laser beam in the first period may be 2.5 W/μsec or less, and the gradient of the output of the laser beam in the second period may be 2.5 W/μsec or more.

In the laser lithotripsy method according to the aspect described above, the gradient of the output of the laser beam in the third period may be 1.25 W/μsec or more and 2.5 W/μsec or less.

In the laser lithotripsy method according to the aspect described above, the gradient of the output of the laser beam in the fourth period may be 2.5 W/μsec or more.

In the laser lithotripsy method according to the aspect described above, the laser beam may be repeatedly emitted without an interval.

In the laser lithotripsy method according to the aspect described above, a repetition frequency of the laser beam may be 1.7 kHz or more and 2.5 kHz or less.

A fourth aspect of the present invention provides a laser lithotripsy method of irradiating a stone in a liquid with a laser beam to crush the stone, the method including: disposing a laser emission end toward the stone; and irradiating the stone with the laser beam of a pulse shape from the laser emission end, the method further including switching an output of the laser beam to a second period in which the output monotonically decreases with a gradient larger than a predetermined gradient after a first period in which the output monotonically increases.

According to the present aspect, the pulsed laser beam is emitted in the state the laser emission end is disposed toward the stone. After the plurality of bubbles are generated continuously from the laser emission end by the laser beam emitted in the first period, the plurality of bubbles are bound, and thus the bubble binding body is formed. The bubble binding body rapidly disappears by the laser beam the output of which is reduced in the second period. Thereby, the suction force is generated, and the stone can be attracted to the laser emission end. Note that the bubble binding body may or may not come into contact with the stone before it disappears. In the case where the bubble binding body comes into contact with the stone before it disappears, it is preferable to cause the bubble binding body to disappear at the moment when the bubble binding body comes into contact with the stone.

Therefore, the stone can be prevented from moving in the direction away from the fiber emission end due to the impact of the laser beam, and the stone can be irradiated with the laser beam within a certain distance from the fiber emission end. Therefore, the suction effect can be effectively used, and the stone can be efficiently irradiated with the laser beam.

In the laser lithotripsy method according to the aspect described above, the laser lithotripsy method may further include maintaining a position of the laser emission end while the laser beam is emitted toward the stone.

With such a configuration, the stone can be efficiently irradiated with the laser beam.

REFERENCE SIGNS LIST 1 laser lithotripsy system
3 laser lithotripsy apparatus
7 display unit
11 stone form recognition unit (calculation unit)
19 image processing processor (image acquisition unit)
23 optical fiber
23a fiber tip
27 waveform control unit (pulse generation unit, output adjustment unit)
S urinary stone (stone)

The invention claimed is:

1. An output adjustment device for a laser lithotripsy apparatus, comprising:
a processor comprising hardware, the processor being configured to control a laser beam source to:
pulse a laser beam; and
adjust a power intensity of the laser beam to:
raise a liquid temperature in a region between a laser emission end and a target; and
after raising the liquid temperature,
monotonically increase the power intensity by a first gradient in a first period to generate a plurality of bubbles that are bound together to form a bubble binding body, the bubble binding body coupling the laser emission end to the target; and
monotonically decrease the power intensity by a second gradient larger than the first gradient in a second period following the first period to cause the bubble binding body to disappear to generate a suction force to attract the target towards the laser emission end.

2. The output adjustment device according to claim 1, wherein the processor is configured to raise the liquid temperature before the first period of monotonically increasing the power intensity.

3. The output adjustment device according to claim 1, wherein before the first period, the processor is configured to adjust the power intensity to:
monotonically increase the power intensity by a fourth gradient in a fourth period to rapidly generate a bubble; and
monotonically decrease the power intensity by a third gradient smaller than the fourth gradient in a third period following the fourth period and before the first period to more gradually increase a size of the bubble until the bubble disappears to generate a suction force to attract the target toward the laser emission end,
wherein the power intensity in the third period and the fourth period raises the liquid temperature prior to the first period.

4. The output adjustment device according to claim 3, wherein:
the third gradient is smaller than a predetermined gradient;
the fourth gradient is larger than the predetermined gradient; and
the predetermined gradient is 2.5 W/μsec.

5. The output adjustment device according to claim 3, wherein the third gradient is 1.25 W/μsec or more and 2.5 W/μsec or less.

6. The output adjustment device according to claim 3, wherein the processor is configured to control the laser beam source to repeat in order of the fourth period, the third period, the first period, and the second period.

7. The output adjustment device according to claim 1, wherein
the first gradient is smaller than a predetermined gradient, the second gradient is larger than the predetermined gradient, and
the predetermined gradient is 2.5 W/μsec.

8. The output adjustment device according to claim 1, wherein the processor is configured to control the laser beam source to alternately repeat the first period and the second period.

9. A suction force generation method executed by a processor, the suction force generation method comprising:
controlling a laser beam source to:
pulse a laser beam; and
adjust a power intensity of the laser beam to:
raise a liquid temperature in a region between a laser emission end and a target; and
after raising the liquid temperature,
monotonically increasing the power intensity by a first gradient in a first period to generate a plurality of bubbles that are bound together to form a bubble binding body, the bubble binding body coupling the laser emission end to the target; and
monotonically decreasing the power intensity by a second gradient larger than the first gradient in a second period following the first period to cause the bubble binding body to disappear to generate a suction force to attract the target towards the laser emission end.

10. The suction force generation method according to claim 9, further comprising:
before the first period, adjusting the power intensity to monotonically increase the power intensity by a fourth gradient in a fourth period to rapidly generate a bubble.

11. The suction force generation method according to claim 10, further comprising:
adjusting the power intensity to monotonically decrease the power intensity by a third gradient smaller than the fourth gradient in a third period following the fourth period and before the first period to more gradually increase a size of the bubble until the bubble disappears to generate a suction force to attract the target towards the laser emission end, wherein the power intensity in the third period and the fourth period raises the liquid temperature prior to the first period.

12. The suction force generation method according to claim 11,
wherein the first gradient to the fourth gradient of the intensity of the laser beam in the first period to the fourth period is in a range of 0.625 to 5.0 W/μs.

13. The suction force generation method according to claim 11,
wherein the third gradient in the third period is 1.25 W/μsec or more and 2.5 W/μsec or less.

14. The suction force generation method according to claim 10,
wherein the fourth gradient in the fourth period is 2.5 W/μsec or more.

15. The suction force generation method according to claim 9,
wherein the first gradient in the first period is 2.5 W/μsec or less, and the second gradient in the second period is 2.5 W/μsec or more.

16. The suction force generation method according to claim 9,
wherein the laser beam is repeatedly emitted without an interval.

17. The suction force generation method according to claim 16,
wherein a repetition frequency of the laser beam is 1.7 kHz or more and 2.5 kHz or less.

18. A method comprising:
inserting an endoscope into a specimen;
disposing a laser emission end toward a target to be attracted;
displaying an image data acquired by the endoscope in a display;
setting a waveform of a laser beam based on the image data; and
controlling a laser beam source to pulse the laser beam and adjusting a power intensity of the laser beam to:
raise a liquid temperature in a region between the laser emission end and the target; and
after raising the liquid temperature,
monotonically increasing the power intensity by a first gradient in a first period to generate a plurality of bubbles that are bound together to form a bubble binding body, the bubble binding body coupling the laser emission end and the target; and
monotonically decreasing the power intensity by a second gradient larger than the first gradient in a second period following the first period to cause the bubble binding body to disappear to generate a suction force to attract the target towards the laser emission end.

19. The method according to claim 18, further comprising:
maintaining a position of the laser emission end while the laser beam is emitted toward the target to be attracted.

20. The method according to claim 18, further comprising:
before the first period, adjusting the power intensity to:
monotonically increase the power intensity by a fourth gradient in a fourth period to rapidly generate a bubble; and
monotonically decrease the power intensity by a third gradient smaller than the fourth gradient in a third period following the fourth period and before the first period to more gradually increase a size of the bubble until the bubble disappears to generate a suction force to attract the target toward the laser emission end,
wherein the power intensity in the third period and the fourth period raises the liquid temperature prior to the first period.

* * * * *